(12) United States Patent
Umezawa

(10) Patent No.: US 10,420,472 B2
(45) Date of Patent: Sep. 24, 2019

(54) APPARATUS AND METHOD

(71) Applicant: CANON KABUSHIKI KAISHA, Tokyo (JP)

(72) Inventor: Kohtaro Umezawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 472 days.

(21) Appl. No.: 15/236,572

(22) Filed: Aug. 15, 2016

(65) Prior Publication Data

US 2017/0055842 A1    Mar. 2, 2017

(30) Foreign Application Priority Data

Aug. 26, 2015 (JP) .................................. 2015-166738

(51) Int. Cl.
*A61B 5/00* (2006.01)
*A61B 5/1455* (2006.01)
*G01N 29/00* (2006.01)
*G06T 5/00* (2006.01)
*G06K 9/00* (2006.01)

(52) U.S. Cl.
CPC ............ *A61B 5/0095* (2013.01); *A61B 5/004* (2013.01); *A61B 5/14552* (2013.01); *G01N 29/00* (2013.01); *G06T 5/002* (2013.01); *G06K 2009/00932* (2013.01); *G06T 2207/30068* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 9,360,551 B2 | 6/2016 | Umezawa et al. | ...... G01S 15/89 |
| 2012/0261427 A1* | 10/2012 | Bates | ................. B65D 81/3869 220/592.17 |
| 2013/0289812 A1* | 10/2013 | Anzicek | .............. B60L 11/1851 701/22 |
| 2015/0216508 A1* | 8/2015 | Iwama | ................. A61B 8/4461 600/438 |
| 2015/0256761 A1 | 9/2015 | Umezawa | .............. H04N 5/243 |
| 2016/0184133 A1 | 6/2016 | Miyasato | .................. A61F 7/08 |

OTHER PUBLICATIONS

K. Maslov et al., "Technical Considerations in Quantitative Blood Oxygenation Measurement Using Photoacoustic Microscopy in Vivo", *Proc. of SPIE*, vol. 6086, pp. 60860R-1 through 60860R-11 (2006).

* cited by examiner

*Primary Examiner* — Ronald Laneau
(74) *Attorney, Agent, or Firm* — Venable LLP

(57) ABSTRACT

An apparatus according to the present invention includes a processor processing characteristic distribution information derived from an acoustic wave generated from an object and which indicates specific values at a plurality of positions inside the object, wherein the processor: sets a first position of interest; acquires first weight distribution information which is related to a plurality of positions including the first position of interest; and acquires a substitute value for a specific value at the first position of interest using the first weight distribution information, the specific value at the first position of interest, and a specific value at a position that differs from the first position of interest among the plurality of positions.

18 Claims, 13 Drawing Sheets

APPARATUS AND METHOD

BACKGROUND OF THE INVENTION

Field of the Invention

The present invention relates to an apparatus and a method.

Description of the Related Art

Recently, research on imaging of functional information of a living organism which is physiological information of the living organism is being pursued in the field of medicine. One technique for imaging functional information is photoacoustic imaging (PAI). With photoacoustic imaging, first, an object is irradiated with pulsed light from a light irradiating unit. When energy of the irradiation light propagated and diffused inside the object is absorbed by a light absorber (such as a blood vessel or skin) in the object, an acoustic wave (a photoacoustic wave) is generated due to a photoacoustic effect. A conversion element then receives the photoacoustic wave and converts the photoacoustic wave into an electrical signal (a received signal). Subsequently, an information processing apparatus analyzes the received signal to acquire a distribution of optical characteristics inside the object. Information beneficial to diagnosis and the like is obtained by converting the distribution of optical characteristics into image data and displaying the image data.

Examples of a distribution of optical characteristics include a distribution of sound pressure generated due to light absorption (a distribution of initial sound pressure) and a distribution of light absorption coefficients. In addition, by irradiating a plurality of pulsed light beams with wavelengths that differ from each other and obtaining a light absorption coefficient for each wavelength, a concentration distribution of a substance present inside the object (a distribution of values related to the concentration of a substance) is obtained. A method of obtaining a distribution of oxygen saturation in blood as a concentration distribution using a difference in light absorption spectra between deoxyhemoglobin and oxyhemoglobin is disclosed in "Technical Considerations in Quantitative Blood Oxygenation Measurement Using Photoacoustic Microscopy in Vivo", Proc. SPIE 6086, Photons Plus Ultrasound: Imaging and Sensing 2006: The Seventh Conference on Biomedical Thermoacoustics, Optoacoustics, and Acousto-optics, 60860R (Mar. 6, 2006).

Non Patent Literature 1: "Technical Considerations in Quantitative Blood Oxygenation Measurement Using Photoacoustic Microscopy in Vivo", Proc. SPIE 6086, Photons Plus Ultrasound: Imaging and Sensing 2006: The Seventh Conference on Biomedical Thermoacoustics, Optoacoustics, and Acousto-optics, 60860R (Mar. 6, 2006)

SUMMARY OF THE INVENTION

In a distribution of characteristics such as a distribution of initial sound pressure, a distribution of absorption coefficients, a distribution of concentration, and a distribution of oxygen saturation, there are parts where values significantly change locally or values are distributed in a patchy fashion due to system noise or a reconstructed artifact. In particular, when distributions of absorption coefficients respectively derived from the light beams having a plurality of wavelengths include noise or the like, a decline in image quality of a distribution of oxygen saturation increases. As a result, image visibility decreases and may prevent an accurate diagnosis from being made. In addition, when an image element unit (a pixel or a voxel) used in calculation is smaller than a structure of a living organism to be drawn, image quality may decline.

The present invention has been made in consideration of the problems described above. An object of the present invention is to reduce the effects of noise and artifacts when displaying characteristic distribution information obtained by photoacoustic imaging.

The present invention provides an apparatus comprising a processor configured to process characteristic distribution information which is derived from an acoustic wave generated from an object irradiated with light and which indicates specific values at a plurality of positions inside the object, wherein the processor is configured to:

set a first position of interest;

acquire first weight distribution information which corresponds to the first position of interest and which is related to a plurality of positions including the first position of interest; and acquire a substitute value for a specific value at the first position of interest using the first weight distribution information, the specific value at the first position of interest, and a specific value at a position that differs from the first position of interest among the plurality of positions.

The present invention also provides a method of processing using characteristic distribution information which is derived from an acoustic wave generated from an object irradiated with light and which indicates specific values at a plurality of positions inside the object, the method comprising the steps of:

setting a first position of interest;

acquiring first weight distribution information which corresponds to the first position of interest and which is related to a plurality of positions including the first position of interest; and acquiring a substitute value for a specific value at the first position of interest using the first weight distribution information, the specific value at the first position of interest, and a specific value at a position that differs from the first position of interest.

According to the present invention, the effects of noise and artifacts when displaying a distribution of characteristic information values obtained by photoacoustic imaging can be reduced.

Further features of the present invention will become apparent from the following description of exemplary embodiments with reference to the attached drawings.

DESCRIPTION OF THE EMBODIMENTS

Figure 1A:
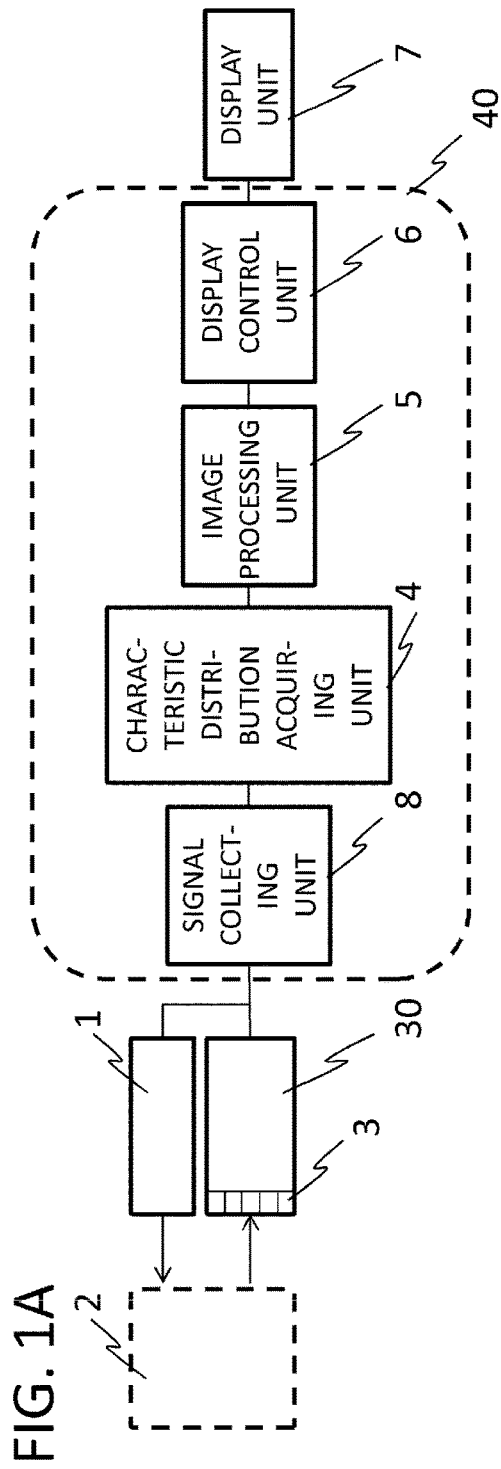
FIGS. 1A and 1B are schematic diagrams showing a configuration of a photoacoustic apparatus and a signal processing unit according to an embodiment.

Hereinafter, preferred embodiments of the present invention will be described with reference to the drawings. However, it is to be understood that dimensions, materials, shapes, relative arrangements, and the like of components described below are intended to be changed as deemed appropriate in accordance with configurations and various conditions of apparatuses to which the present invention is to be applied. Therefore, the scope of the present invention is not intended to be limited to the embodiments described below.

The present invention relates to a technique for detecting an acoustic wave propagating from an object and generating and acquiring characteristic distribution information of the inside of the object. Accordingly, the present invention can be considered an object information acquiring apparatus or a control method thereof, or an object information acquiring method or an object information processing method. The present invention can also be considered a program that causes an information processing apparatus including hardware resources such as a CPU and a memory to execute these methods or a storage medium storing the program.

The object information acquiring apparatus according to the present invention includes an apparatus (a photoacoustic apparatus) utilizing a photoacoustic effect in which an acoustic wave generated inside an object by irradiating the object with light (an electromagnetic wave) is received and characteristic distribution information of the object is acquired as image data. Characteristic distribution information according to the present invention refers to information on specific values at a plurality of two-dimensional or three-dimensional positions which is generated using a signal obtained by receiving a photoacoustic wave.

A specific value according to the present invention is a value reflecting an absorption rate of optical energy. For example, a generation source of acoustic waves generated by light irradiation, initial sound pressure inside an object, or optical energy absorption density or an optical energy absorption coefficient derived from initial sound pressure can be considered "specific values based on light absorption" or "optical characteristic values inside an object". Specific values include concentration information of substances constituting tissue.

Concentration information includes a value related to concentration of a substance present inside an object which is obtained using a received signal based on light absorption corresponding to a plurality of wavelengths. Specific examples of concentration information include oxygen saturation, total hemoglobin concentration, oxyhemoglobin concentration, and deoxyhemoglobin concentration. In addition, concentration information may be glucose concentration, collagen concentration, melanin concentration, a volume fraction of fat or water, or the like. Furthermore, concentration information also includes values obtained by weighting the concentration described above with intensity of an absorption coefficient or the like.

An acoustic wave according to the present invention is typically an ultrasonic wave and includes an elastic wave which is also referred to as a sonic wave or an acoustic wave. An electrical signal transformed from an acoustic wave by a probe or the like is also referred to as an acoustic signal. However, descriptions of an ultrasonic wave and an acoustic wave in the present specification are not intended to limit a wavelength of the elastic waves. An acoustic wave generated by a photoacoustic effect is referred to as a photoacoustic wave or an optical ultrasonic wave. An electrical signal derived from a photoacoustic wave is also referred to as a photoacoustic signal.

Primary objects of the photoacoustic apparatuses according to the embodiments presented below are to diagnose a malignant tumor, a vascular disease and the like of a human or an animal, to perform a follow-up observation of chemotherapy, and the like. Therefore, an object is assumed to be a part of a living organism or, more specifically, a part of a human or an animal (such as a breast, an organ, the circulatory system, the digestive system, a bone, a muscle, and fat). Substances that are examination objects include hemoglobin, glucose, as well as water, melanin, collagen, and lipids which are present in the body. Furthermore, any substance with a characteristic light absorption spectrum including contrast agents such as indocyanine green (ICG) administered into the body may suffice.

First Embodiment (Overall Apparatus Configuration)

FIG. 1A is a schematic diagram showing a configuration of a photoacoustic apparatus according to the present embodiment. The photoacoustic apparatus according to the present embodiment is at least provided with a light irradiating unit 1, a probe 30 including a conversion element 3 which receives a photoacoustic wave, and a processor 40 which performs processing using a received signal output from the conversion element 3.

Light output from the light irradiating unit 1 is irradiated on an object 2 via a light propagating member (not shown) such as a fiber or a lens. When obtaining concentration distribution information, pulsed light beams with wavelengths that differ from each other are irradiated at different timings. The irradiated light is propagated and diffused inside the object and is absorbed by a substance present in the object. A substance that absorbs light (light absorbers) absorbs energy of the respective pulsed light beams and generates respective photoacoustic waves. The generated photoacoustic waves propagate inside the object and reach the conversion element 3. The conversion element 3 is favorably acoustically matched with the object by an acoustic matching material or the like.

Each of the plurality of conversion elements 3 receives a photoacoustic wave and outputs a received signal in a time series. The output received signal is sequentially input to the processor 40 for each irradiated pulsed light. Using the input received signal, the processor 40 generates characteristic distribution information based on light absorption inside the object. In addition, the processor 40 generates image data based on the generated distribution and displays an image on a display unit 7. When the photoacoustic apparatus is an apparatus which sets a relatively small object as an examination object such as a photoacoustic microscope, the probe 30 may only include one conversion element 3. On the other hand, when a relatively large object such as a breast is an examination object, the probe 30 favorably includes a plurality of conversion elements 3. Moreover, the light irradiating unit 1 may be provided separately from the photoacoustic apparatus according to the present embodiment. In addition, the probe 30 may be provided separately from the photoacoustic apparatus according to the present embodiment.

(Internal Configuration of Processor 40)

The processor 40 according to the present embodiment is provided with a signal collecting unit 8, a characteristic distribution acquiring unit 4, an image processing unit 5, and a display control unit 6. The signal collecting unit 8 collects analog received signals in a time series respectively output from the plurality of conversion elements 3 for each channel and performs signal processing such as amplification of a received signal, A/D conversion of an analog received signal, storing of a digitalized received signal, and signal correction. Moreover, while the respective embodiments of the present invention are configured such that various processing blocks are included in a processor, an arrangement of processing blocks is not limited thereto.

Using the received signal output from the signal collecting unit 8, the characteristic distribution acquiring unit 4 generates characteristic distribution information based on light absorption inside the object. Here, an example in which a distribution of initial sound pressure is obtained as a characteristic distribution based on light absorption will be described. An absorption coefficient $\mu_a$ at a given position (i, j, k) inside the object can be acquired according to expression (1), where (i, j, k) represents coordinates inside the object.

[Math. 1]

$$P = \Gamma \cdot \mu_a \cdot \phi \quad (1)$$

In expression (1), P denotes initial sound pressure (generated sound pressure) at the position (i, j, k), $\Gamma$ denotes the Grüneisen constant, and $\phi$ denotes an amount of light having reached the position (i, j, k).

Moreover, initial sound pressure P at the position (i, j, k) in three-dimensional spatial coordinates is obtained by applying a filter for correcting a band of the probe to the received signal of each channel output from the signal collecting unit 8 and then performing image reconstruction. Known methods such as universal back-projection (UBP), filtered back-projection (FBP), and a phasing addition process can be used for image reconstruction.

A distribution of initial sound pressure can be acquired from initial sound pressure at each position inside the object as obtained by the image reconstruction process. The distribution of initial sound pressure may be three-dimensional data (set data of voxels) corresponding to a given region in the object or two-dimensional data (set data of pixels) corresponding to one section in the three-dimensional data.

Moreover, an image reconstruction process need not necessarily be performed in cases of a light-focusing photoacoustic microscope or an acoustic-focusing photoacoustic microscope using a focusing probe. In this case, a photoacoustic wave is received at each position to which the probe 30 and a light irradiating spot are relatively moved with respect to the object 2 by a scanning mechanism (not shown). In addition, after performing envelope detection on the received signal with respect to a time change, a time axis direction in a signal for each light pulse is converted into a depth direction and plotted on spatial coordinates. Distribution data can be constructed by performing these steps for each scanning position.

When calculating a distribution of absorption coefficients with the characteristic distribution acquiring unit 4, expression (1) is used on a distribution of initial sound pressure to perform correction in accordance with light quantity distribution. Moreover, the Grüneisen constant can be regarded as constant. A light quantity distribution is obtained based on a distribution of light irradiated on the object by a calculation which takes light propagation inside the object into consideration. In doing so, the calculation may be performed by considering a shape of the object. As a simple method, a light quantity distribution determined in advance based on degrees of general attenuation and scattering may be used. When a deviation of positions or a deformation occurs while measurement is being performed a plurality of times, positioning according to known methods such as affine transformation and free-form deformation (FFD) may be performed. The characteristic distribution acquiring unit 4 outputs the obtained characteristic distribution information to the image processing unit 5.

(Image Processing Unit 5)

The image processing unit 5 sets a mask on the characteristic distribution information output from the characteristic distribution acquiring unit 4 and, after statistically processing intensity based on data inside the mask, performs mapping. In this case, mapping refers to substituting a specific value with a value suitable for display. As the characteristic distribution output from the characteristic distribution acquiring unit 4, a distribution of absorption coefficients of the object such as that described below is preferable. However, a distribution of initial sound pressure may be used.

(Creating Mask)

Figure 3:
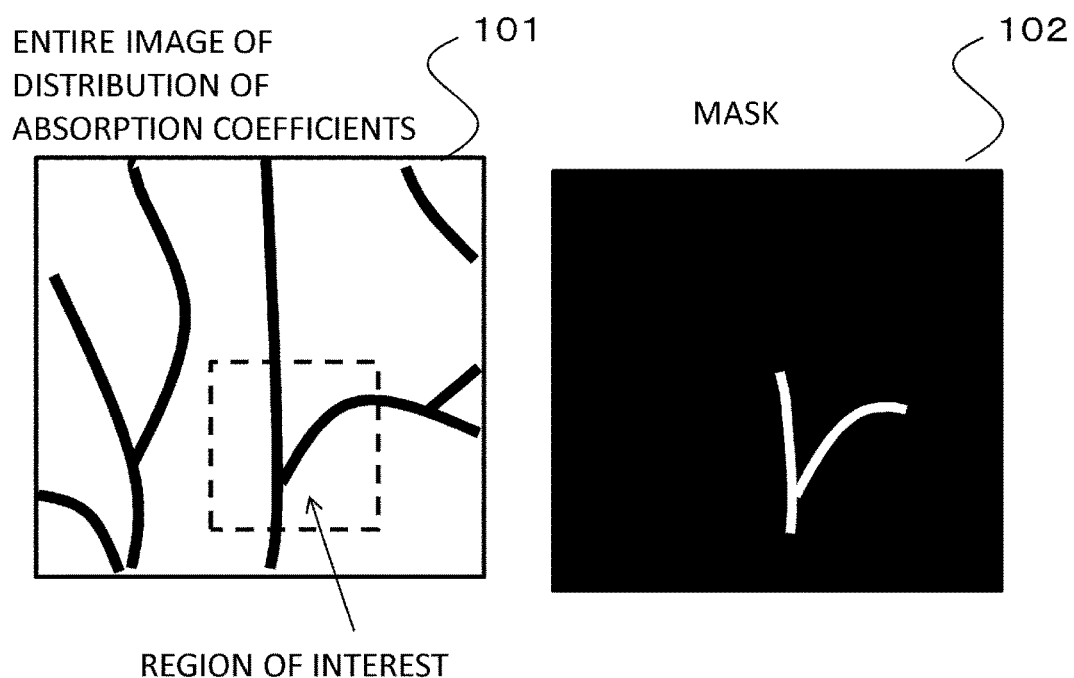
FIG. 3 is a schematic diagram showing an operation of a processor according to the embodiment.

FIG. 3 shows an example of a mask applied to a distribution of absorption coefficients. Reference numeral 101 denotes an image of an entire distribution of absorption coefficients. An operator sets a region of interest in the image. Reference numeral 102 denotes a mask to be applied to a blood vessel portion inside the set region of interest. While two-dimensional images are shown in this case for the sake of convenience, an actual distribution of absorption coefficients or an actual mask may be three-dimensional voxel data. In addition, setting a region of interest is not essential and the entire distribution of absorption coefficients may be set as a processing object. Furthermore, an entirety of the distribution may be set as a region of interest.

Methods of setting a region of interest include automatically extracting a vicinity of a region where intensity of an absorption coefficient is high. Methods of automatically extracting a region of interest include a method in which a threshold of the intensity of an absorption coefficient is set to the apparatus and a region containing a region having a value equal to or larger than the threshold is extracted. In addition, the apparatus may automatically extract a tumor position or a blood vessel region. Alternatively, instead of automatic extraction, a part of or all of an image may be set to the apparatus in advance as a region of interest. Furthermore, the operator may set a region of interest using inputting means (for example, a mouse or a keyboard).

The mask shown in FIG. 3 is a binarization of a living organism structure portion (such as a blood vessel) in the region of interest. A mask that is a multiplexed value may be used instead of a binarized mask. Methods of binarization or value multiplexing include setting a threshold to intensity of an absorption coefficient and extracting a region with intensity exceeding the threshold as a blood vessel or segmenting a region in accordance with the threshold. Examples of value multiplexing include a method of determining a region with a characteristic information value that is equal to or larger than a prescribed threshold as a blood vessel and determining a region with a value that is equal to or smaller than a noise level as zero. In addition, an adaptive binarization process or an adaptive value multiplexing process in which a threshold is adaptively set in accordance with a region can be used. Furthermore, arbitrary methods such as a graph cut method in which an image is segmented or a method in which the operator interactively specifies a blood vessel region can be used.

The mask may be created from a characteristic distribution of one wavelength among a plurality of wavelengths. In addition, a plurality of characteristic distributions obtained for each wavelength may be composited by calculating an arithmetic mean or the like and a mask may be created based on the composite characteristic distribution. Alternatively, a sum set or a product set of all created masks may be used as the mask. A wide region is determined as a blood vessel when using a sum set while a region with a high probability of being a blood vessel is extracted when using a product set.

A distribution other than a distribution of absorption coefficients may be used as basic data for creating the mask. For example, a distribution of absorption coefficient intensity ratios obtained by normalizing a distribution of absorption coefficients by intensity, a weight distribution of abundance ratios of substances attributable to a living organism, a distribution of initial sound pressure, and a distribution of optical energy absorption density can also be used. In addition, known blood vessel extraction methods may be used in order to determine whether or not a given position inside the object is a blood vessel. For example, modalities other than photoacoustic measurement such as ultrasonic measurement, infrared measurement, and visible light measurement can be used.

In this description, the term "mask" is used in order to determine a specific value to be an object of value substitution from characteristic distribution information (absorption coefficient distribution information, oxygen saturation distribution information, or the like). In this case, a mask can be considered a weight distribution in which a specific value that is a substitution object is 1 and a specific value that is not a substitution object is 0. In other words, the image processing unit 5 selects specific values within the mask or, in other words, specific values with a weight of 1 and calculates an average value (a statistical value) of the selected specific values. Moreover, a weight distribution is not limited to a binary distribution and may be a gradual distribution as will be described later. In addition, a mode in which each value in a weight distribution is not evaluated and all values included in characteristic distribution information are set as substitution objects is also included in the present invention.

(Processing Using Mask)

A method of statistically processing intensity based on data within a mask will now be described. In the present embodiment, a representative value of data in the mask is calculated and all data in the mask is mapped (substituted) by the representative value. In the present embodiment, each position in the mask is set as a position of interest and considered a substitution object. In order to reduce the effect of a noise region where dispersion is large, a mode of data in the mask may be used as the representative value. Alternatively, a mean or a median may be used as the representative value. In this case, the effect of noise is favorably reduced by eliminating values with large dispersion. By performing correction using characteristic information values that are not substitution object values, noise can be effectively reduced. Other representative value calculation methods may also be used as long as the effect of noise can be reduced. For example, when data in the mask is expressed as a histogram, after eliminating values outside $3\sigma$ of the distribution, a mode, a mean, or a median may be calculated. In addition, a representative value may be calculated after eliminating a region where intensity of the histogram is extremely small or large. In other words, a weight may be determined based on dispersion from a specific value at a processing object voxel. Moreover, $3\sigma$ is simply an example of a target related to disperse values and an indicator used for eliminating extreme values is not limited thereto.

As a method of mapping a representative value, all data in the mask is substituted by the representative value in the present embodiment. Other mapping methods include a method of assigning a representative value to one voxel being set as a calculation object. Subsequently, a distribution of absorption coefficients is created from data in the mask substituted by the representative value and from data outside of the mask. Accordingly, a distribution of absorption coefficients in which the inside of a masked region is substituted by the representative value is obtained. When performing photoacoustic measurement at a plurality of wavelengths, a mask creating process or a mapping process may be performed for each wavelength or a mask derived from any one wavelength may be applied to other wavelengths. In addition, a plurality of masks obtained for each wavelength may be composited by averaging or by calculating a sum set. Moreover, although the substitution of the inside of a mask with a representative value has been described, the preparation of a mask is not essential in information processing. The present invention can be applied to any process as long as the process sets a group (including an entire distribution) of given characteristic information values and substitutes the values.

The image processing unit 5 sets a mask on the characteristic distribution output from the characteristic distribution acquiring unit 4 and, after statistically processing intensity based on data in the mask, performs mapping. A signal after value substitution is output to the display control unit 6.

The display control unit 6 generates image data to be displayed by the display unit 7 based on the distribution of absorption coefficients generated by the characteristic distribution acquiring unit 4 and distribution data generated by the image processing unit 5. Specifically, image processing such as brightness conversion, distortion correction, and logarithmic compression is performed based on the distribution data. In addition, display control such as arranging and displaying various display items together with the distribution data is performed.

(Processing Flow of Processor 40)

Figure 2:
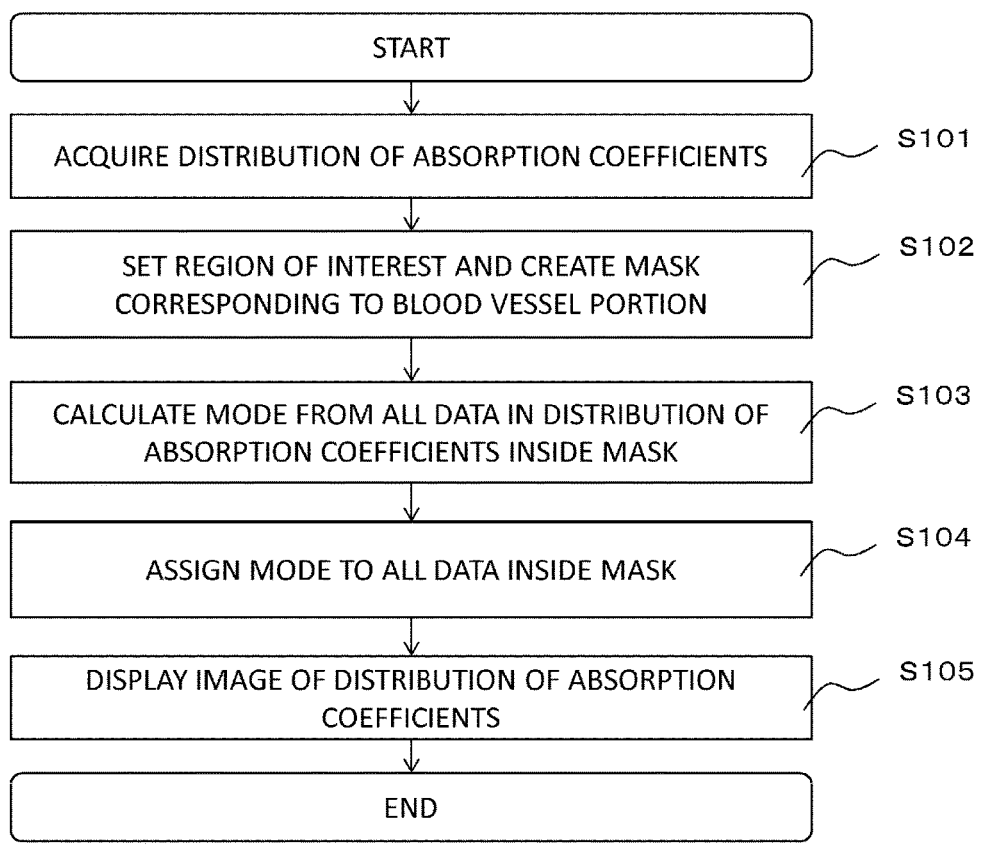
FIG. 2 is a flow chart showing an operation of a processor according to the embodiment.

A processing flow of the processor 40 will be described with reference to FIG. 2. The present flow starts from a state where received signals are sequentially input from the probe for each pulse of irradiated light to the signal collecting unit 8 in the processor 40 and processing such as A/D conversion and amplification has been performed by the signal collecting unit 8.

In step S101, using a received signal due to irradiated laser light with a wavelength $\lambda_1$, the characteristic distribution acquiring unit 4 calculates a distribution of initial sound pressure of the wavelength $\lambda_1$ and calculates a distribution of absorption coefficients from a distribution of amounts of irradiated light.

In step S102, the image processing unit 5 sets a region of interest in the distribution of absorption coefficients. A blood vessel portion is binarized inside the set region of interest and a mask is created. As a method of binarization, a threshold of intensity of absorption coefficients is set and a region with a value equal to or larger than the threshold is assumed to be a blood vessel portion. In step S103, a representative value (in this case, a mode) is calculated from all data in the distribution of absorption coefficients inside the mask set in S102.

In step S104, the obtained representative value is assigned to all data inside the mark while the original distribution of absorption coefficients is used for data outside of the mask. Accordingly, a distribution of absorption coefficients in which only the region inside the mask is substituted by the representative value is obtained. In step S105, the display control unit 6 generates image data of the distribution of absorption coefficients calculated by the image processing unit 5 and displays the image data on the display unit 7.

As described above, in the present embodiment, a distribution of absorption coefficients can be preferably displayed even when the distribution of absorption coefficients contains noise or artifacts.

Moreover, an object of the present embodiment is not limited to a blood portion inside a blood vessel. For example, an object of the present embodiment may be a blood vessel wall, a lymphatic vessel, muscle tissue, mammary gland tissue, adipose tissue, or an aggregate of substances (for example, a molecular targeting drug as a contrast agent) injected from the outside.

Next, specific configuration examples of each component of the present embodiment will be described.

(Light Irradiating Unit 1)

The light irradiating unit 1 is favorably a pulsed light irradiating unit capable of generating pulsed light in the order of nanoseconds to microseconds. Specifically, a pulse width of 1 nanosecond or more and 100 nanoseconds or less is preferably used. In addition, a wavelength in a range of 400 nm or more and 1600 nm or less is used. In particular, when performing imaging of deep portions of a living organism, light in a wavelength band referred to as a "biological window" (a wavelength band with less absorption by background tissue of a living organism) is used. Specifically, a wavelength region of 700 nm or more and 1100 nm or less is favorable. On the other hand, when performing imaging of a blood vessel in a vicinity of a surface of a living organism at high resolution, a visible light region is favorably used. However, regions of terahertz waves, microwaves, and radio waves can also be used. In order to perform wavelength conversion, a variable-wavelength laser using a medium having a gain in a wide region may be used or a plurality of light sources which irradiate light with mutually different wavelengths may be used in combination.

A laser is favorable as the light irradiating unit 1. As the laser, various lasers such as a solid-state laser, a gas laser, a dye laser, and a semiconductor laser can be used. A pulse laser such as a Nd:YAG laser or an alexandrite laser is particularly favorable. In addition, a Ti:Sa laser using Nd:YAG laser light as excitation light or an optical parametric oscillator (OPO) laser may be used. Furthermore, a light-emitting diode, a flash lamp, or the like may be used in place of a laser.

Pulsed light output from the light irradiating unit is favorably guided to the object by a member (an optical member) which propagates light such as an optical fiber, a lens, a mirror, and a diffuser plate. In addition, when guiding the pulsed light, a spot shape or a light density of the pulsed light can be changed using these optical members.

(Probe 30)

The probe 30 includes one or more conversion elements 3. As the conversion element 3, any conversion element including a piezoelectric element using a piezoelectric phenomenon such as lead zirconate titanate (PZT), a conversion element using optical resonance, and a capacitance-type conversion element such as a CMUT may be used as long as an acoustic wave can be received and converted into an electrical signal. When a plurality of conversion elements 3 are provided, the conversion elements 3 are favorably arranged on a flat surface or a curved surface in an arrangement referred to as a 1 D array, a 1.5 D array, a 1.75 D array, or a 2 D array. When arranging the conversion elements in a curved surface, a supporter with a cup shape or a spherical crown shape is favorably used. Providing a high sensitivity region where directional axes (directions of high receiving sensitivity) of the respective conversion elements converge improves image accuracy.

In addition, the probe 30 may be configured to be mechanically movable with respect to the object or may be a handheld probe 30 which is grasped by the operator when moved. In the case of mechanical scanning, a scanning mechanism using an XY stage, a motor, an actuator, or the like can be used. In the case of a photoacoustic microscope, the probe 30 is favorably a focusing probe which mechanically moves along a surface of the object. In addition, favorably, an irradiation position of irradiation light and the probe 30 move in synchronization with each other. Furthermore, an amplifier which amplifies an analog signal output from the conversion element 3 may be provided inside the probe 30.

The object is favorably held by a holding member capable of transmitting light and acoustic waves. Accordingly, since an object shape is stabilized, accuracy of calculation of a specific value improves. Examples of holding methods include a method of compressing the object with a plate and a method of holding a suspended breast using a cup-shaped holding member. Preferable materials of the holding member include acrylic and polymethylpentene. In addition, when using a holding member, a matching material for enhancing an acoustic matching effect is favorably arranged between the holding member and the probe and between the object and the holding member. When a holding member is not used, the matching material is favorably arranged between the object and the probe. Examples of matching material include water, castor oil, and ultrasonic gels.

(Display Unit 7)

For the display unit 7, a display such as a liquid crystal display (LCD), a cathode ray tube (CRT), and an organic EL display can be used. Moreover, instead of providing the display unit 7 as a component of the object information acquiring apparatus according to the present embodiment, the display unit 7 may be separately provided and connected to the object information acquiring apparatus.

(Processor 40)

The signal collecting unit 8 can use a circuit generally referred to as a data acquisition system (DAS). Specifically, the signal collecting unit 8 includes an amplifier which amplifies a received signal, an A/D converter which digitalizes an analog received signal, and a memory such as a FIFO, a RAM, or the like which stores a received signal.

As the characteristic distribution acquiring unit 4 and the image processing unit 5, a processor such as a CPU, an MPU, and a graphics processing unit (GPU) can be used. In addition, an operation circuit such as a field programmable gate array (FPGA) chip may be used. Moreover, the processor 40 is not limited to a configuration having a single processor or an operation circuit and may be constituted by a plurality of processors or operation circuits. Furthermore, a memory for storing a received signal, specific value information, a distribution of specific value information, and the like may be provided. The memory is typically constituted by a storage medium such as a ROM, a RAM, and a hard disk. Moreover, the memory is not limited to a configuration having a single storage medium and may be constituted by a plurality of storage media. The memory is typically constituted by one or more storage media such as a ROM, a RAM, and a hard disk.

Figure 1B:
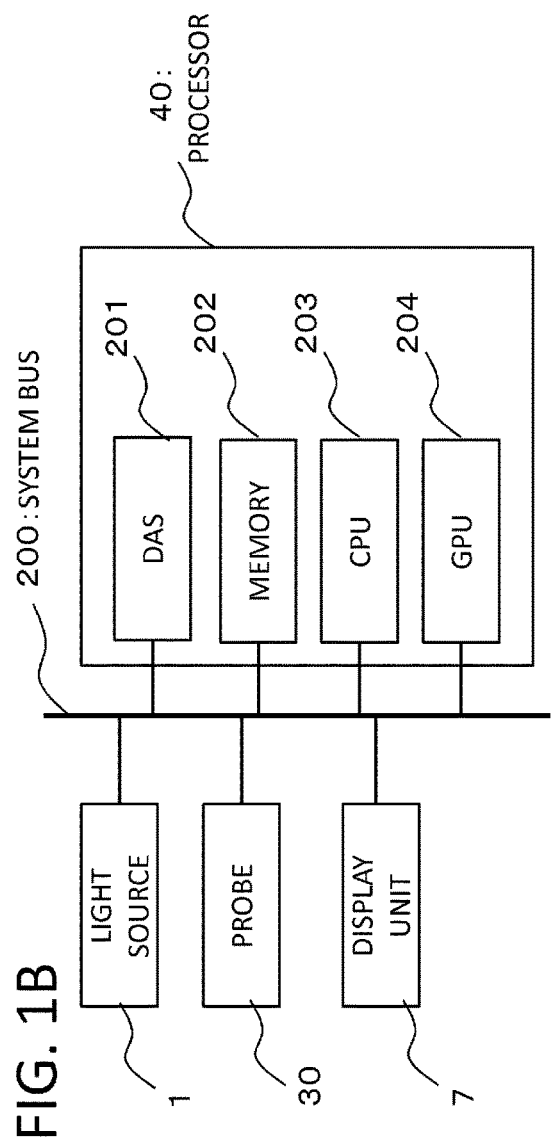

FIG. 1B is a schematic diagram showing an example of a structure of the processor 40 and a relationship between the processor 40 and external devices. The processor 40 includes a DAS 201, a memory 202, a CPU 203, and a GPU 204. The DAS 201 performs one function of the signal collecting unit 8 according to the present embodiment. A digital signal transferred from the DAS 201 is stored in the memory 202.

The CPU 203 performs a part of functions of the characteristic distribution acquiring unit 4, the image processing unit 5, and the display control unit 6 according to the present embodiment. Specifically, the CPU 203 controls respective constituent blocks via a system bus 200. In addition, the CPU 203 can perform signal processing such as an integration process and a correction process on the digital signal stored in the memory 202. Furthermore, the CPU 203 rewrites the digital signal after the signal processing into the memory 202 to be supplied to the GPU 204 for generating distribution data.

The GPU 204 performs a part of functions of the characteristic distribution acquiring unit 4, the image processing unit 5, and the display control unit 6 according to the present embodiment. Specifically, the GPU 204 creates distribution data using the digital signal subjected to signal processing by the CPU 203 and written into the memory 202. In addition, the GPU 204 can create image data by applying various image processing such as brightness conversion, distortion correction, and segmentation of a region of interest to the created distribution data. Moreover, similar processing can also be performed by the CPU 203. The configuration described above is simply an example and any information processing apparatus can be used as long as the information processing apparatus is capable of executing the signal processing and control processes according to the present invention.

(Simulation)

Figure 4:
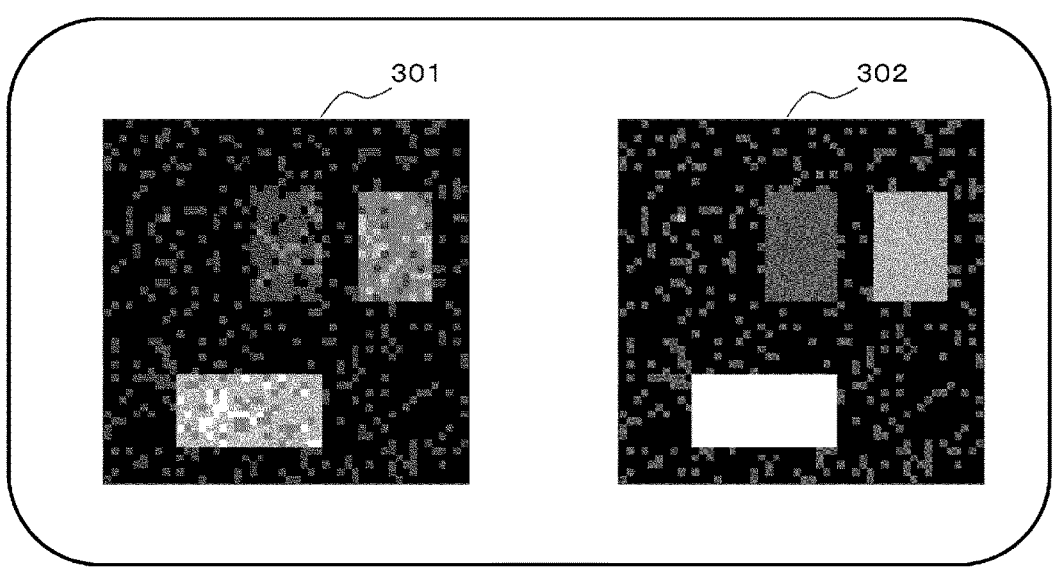
FIG. 4 is a diagram showing a simulation according to the embodiment.

FIG. 4 shows a result of verification by a simulation using the present method. Reference numeral 301 on the left side of the diagram denotes a distribution of absorption coefficients. Voxels with an absorption coefficient intensity equal to or higher than a prescribed threshold have been extracted and set as the inside of a mask through a process performed by the image processing unit 5. The diagram shows that there are three regions where the intensity is equal to or larger than the threshold and which are assumed to be blood vessels. On the other hand, regions where the intensity is lower than the prescribed value are considered to be outside of the mask and are shown with a dark color in the diagram. In the state prior to processing, noise is observed over the entire image.

Meanwhile, reference numeral 302 on the right side of the diagram denotes a distribution of absorption coefficients after being processed by the image processing unit 5. In this case, for each of the three regions, an average value inside the mask is used as a representative value. In addition, when a single mask is shaped so as to combine a plurality of blood vessels, the mask can be divided into a plurality of masks. Conversely, a plurality of masks may be processed collectively. The image after processing reveals that noise has been reduced and no significant changes have been made to intensity. Moreover, a method of displaying images is not limited to a method in which images before and after processing are placed side by side as in FIG. 4. For example, a process button may be provided in the screen and, when the button is pressed using inputting means such as a mouse, the display may be switched to the processed image. In addition, images may be switched after a prescribed period of time. Furthermore, images or masks representing a plurality of wavelengths may be arranged side by side. Moreover, a button for switching between correction methods may be provided. In addition, a physical button may be provided in place of an image UI.

[First Practical Example]

In a first practical example, a phantom simulating a breast is used as an object. Light is irradiated from a light source through a holding member made of polymethylpentene which holds the object. The probe 30 receives a photoacoustic wave through the holding member. The probe 30 is a 2D probe including a plurality of conversion elements in a 1 MHz±40% frequency band.

In the present practical example, first, the object is irradiated with pulsed light having a wavelength of 797 nm from the light irradiating unit 1. The probe 30 receives a photoacoustic wave, converts the photoacoustic wave into an electrical signal, and outputs the electrical signal. After being subjected to digital conversion and amplification, the received signal is subjected to image reconstruction by universal back-projection at the processor 40. Accordingly, a three-dimensional distribution of initial sound pressure of one pulse is obtained. In the obtained distribution of initial sound pressure, only a region of a distribution of irradiated pulsed light has been reconstructed. In this case, the obtained distribution of initial sound pressure is constituted by 160 voxels vertically, 160 voxels horizontally, and 200 voxels in a height direction. A distribution of absorption coefficients can be calculated by correcting the obtained distribution of initial sound pressure based on light quantity distribution.

Next, the processor 40 sets a part of the distribution of absorption coefficients as a region of interest and creates a mask for a blood vessel inside the region of interest. In this case, a maximum intensity of absorption coefficient values is obtained and a mask is created using a value that is half of the maximum intensity as a threshold. Subsequently, the created mask is applied to the distribution of absorption coefficients to determine whether or not each position in the region of interest is a blood vessel. As a result, a voxel having intensity equal to or higher than the threshold is extracted as a blood vessel. Next, a mode of intensities of the extracted blood vessel portion is calculated as a representative value. The value of each voxel in the blood vessel portion is then substituted by the representative value. By combining an image of the blood vessel portion to which the representative value is assigned with an image of the outside of the mask, a distribution of absorption coefficients in which the representative value is assigned to the blood vessel portion inside the region of interest is obtained.

For example, in the case of FIG. 4, while a representative value (a substitute value) is favorably calculated for each of the three blood vessel regions, one substitute value for each image obtained by calculating a mode from inside the entire mask may be applied to all blood vessel regions. Alternatively, sub regions may be set to each region in accordance with a size and shape of the region.

As described above, in the present practical example, a representative value is calculated and assigned using a signal of the inside of a living organism structure such as a blood vessel. As a result, even if a distribution of absorption coefficients contains noise or artifacts, calculation accuracy of an absorption coefficient value in a blood vessel portion improves.

Second Embodiment

Next, a second embodiment will be described. Since the present embodiment uses an apparatus configuration approximately similar to that of the first embodiment, a detailed description of each component will be omitted. The following description will focus on portions that differ from the first embodiment such as a part of contents of processing by the processor 40.

Figure 5:
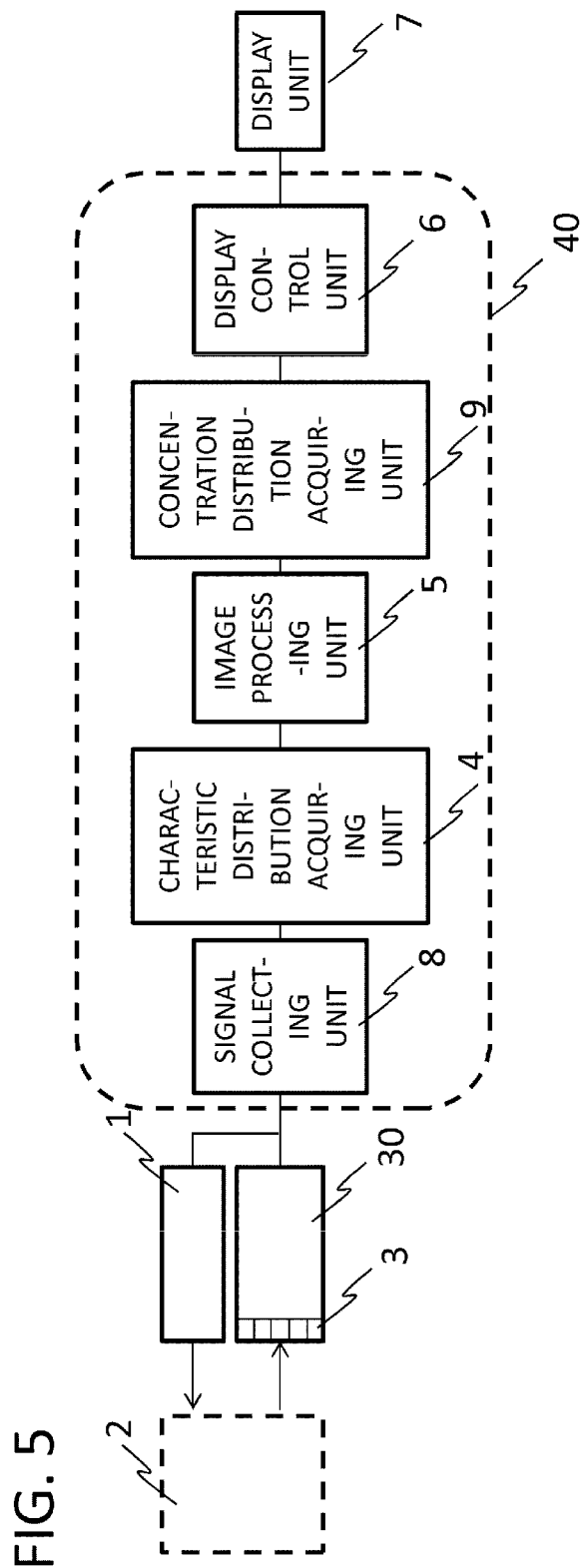
FIG. 5 is a schematic diagram showing a configuration of a photoacoustic apparatus according to another embodiment.

FIG. 5 is a schematic diagram showing a configuration of a photoacoustic apparatus according to the present embodiment. The apparatus calculates a distribution of oxygen saturation from distributions of absorption coefficients of a plurality of wavelengths. In addition, even if the distribution of absorption coefficients of each wavelength contains noise or artifacts, the effect of the noise or the artifacts can be reduced from a signal inside a living organism structure region. As a result, a distribution of oxygen saturation for which the effect of noise or artifacts has been reduced in a living organism structure region can be calculated.

(Image Processing Unit 5)

In a similar manner to the first embodiment, the image processing unit 5 sets a mask on the characteristic distribution output from the characteristic distribution acquiring unit 4 and, after statistically processing intensity based on data in the mask, performs mapping. In the present embodiment, contents of processing when a plurality of characteristic distributions are input will be described.

Among distributions of absorption coefficients at the wavelength $\lambda_1$ and the wavelength $\lambda_2$ as generated by the characteristic distribution acquiring unit 4, a region of interest is set in the distribution of absorption coefficients for the wavelength $\lambda_1$ and a mask for a blood vessel portion inside the region of interest is created. As a method of creating the mask, a known blood vessel extraction method using a line-enhancing filter and a region growing method on the distribution of absorption coefficients is used. The obtained mask is applied to both distributions of absorption coefficients of the wavelength $\lambda_1$ and the wavelength $\lambda_2$ to calculate distributions of absorption coefficients of the two masked wavelengths.

Figure 6:
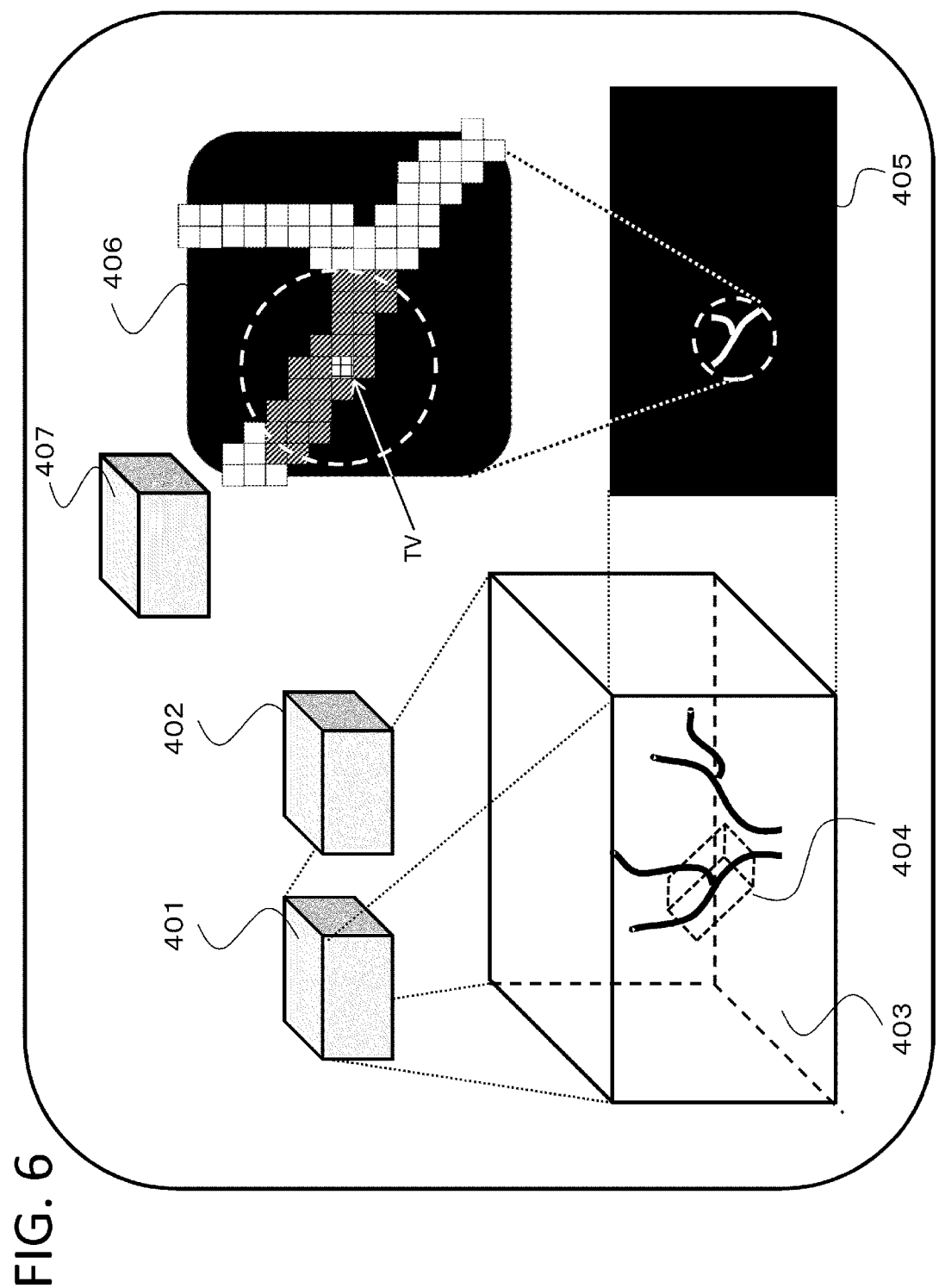
FIG. 6 is a schematic diagram showing an operation of a processor according to the embodiment.

Next, a method of statistical processing will be described with reference to FIG. 6. FIG. 6 is a conceptual diagram for showing data handled inside the processor 40 and a procedure of signal processing. Therefore, such a diagram need not necessarily be displayed on the display unit.

Reference numeral 401 denotes a three-dimensional distribution of absorption coefficients of the wavelength $\lambda_1$ and reference numeral 402 denotes a three-dimensional distribution of absorption coefficients of the wavelength $\lambda_2$. Reference numeral 403 is a conceptual diagram focusing on the distribution of absorption coefficients denoted by reference numeral 401 and indicates that absorption coefficient values in a blood vessel portion have increased. In actual signal processing, the conceptual diagram is used as a result of comparing intensity of each voxel with a threshold. Reference numeral 404 denotes a region of interest set in a blood vessel portion. The region of interest can be set by an input from the operator using an UI such as a mouse or a keyboard or by an automatic setting in accordance with a prescribed rule. A wider range of the object can be set as a processing object by sequentially moving the region of interest.

Reference numeral 405 denotes a side view of a mask corresponding to the distribution of absorption coefficients denoted by reference numeral 403. Reference numeral 406 denotes an enlarged view of a portion enclosed by a white dashed line in the mask denoted by reference numeral 405. In reference numeral 406, a voxel of interest (denoted by reference character TV) is depicted as a shaded voxel. A voxel data region within a range of equal distance (the white dashed line in reference numeral 406) from the voxel of interest is depicted by hatchings. Although the inside of a sphere at an equal distance from the voxel of interest is actually a processing object in three-dimensional data, a two-dimensional representation is given instead for the sake of brevity. In the present embodiment, with a focus on each voxel in the mask, statistical processing is performed using voxel data in a region in a vicinity of the voxel in focus and for which a value is available.

Reference numeral 407 denotes an empty three-dimensional distribution prepared for assigning a newly calculated distribution of absorption coefficients. As a method of statistical processing, a method of calculating an absorption coefficient intensity of the voxel of interest (TV) denoted by reference numeral 406 will be described. First, voxel data in the vicinity of the voxel of interest is extracted and a representative value is obtained. The obtained representative value is assigned to a corresponding voxel in the prepared empty three-dimensional distribution. Next, similar processing is performed by regarding another voxel as a voxel of interest. In this case, the calculated value is assigned to the prepared empty three-dimensional distribution because intensity of a voxel once obtained by calculating a representative value is not used when obtaining intensity of other voxels.

A mode, a median, or a mean is desirable as the representative value (the substitute value). In addition, there is a method in which a threshold of intensity is set with respect to extracted voxel data and values equal to or smaller than the threshold are not used when calculating a representative value. Furthermore, a process may be performed in which values with a dispersion of $3\sigma$ or more as compared to an average of the extracted voxel data are eliminated and then a mode, a median, or a mean is calculated. For example, when calculating an average value after eliminating values with a dispersion of $3\sigma$ or more from an average of the extracted voxel data, first, voxel data in the vicinity of the voxel of interest is extracted and an average value and a standard deviation of the extracted voxel data are obtained. Next, values with a dispersion of $3\sigma$ or more from the average value of the extracted voxel data are eliminated. An average value is then calculated in the data after eliminating voxel values with high dispersion values. A distribution of absorption coefficients is obtained by assigning the calculated average value to the voxel of interest. Accordingly, extreme outliers can be eliminated.

In this manner, assignment (substitution) of values of all voxel data in the mask is performed. On the other hand, original values are used for voxels outside of the mask. As a result, a distribution of absorption coefficients with greater legibility in which values of voxels with a high probability of corresponding to the inside of a blood vessel are processed can be acquired.

As described above, with the image processing unit 5, a distribution of absorption coefficients in which the effects of noise and artifacts have been reduced is obtained by substituting a value of each voxel in a mask.

(Concentration Distribution Acquiring Unit 9)

A concentration distribution acquiring unit 9 acquires concentration distribution information using distribution information such as initial sound pressure distribution information and absorption coefficient distribution information generated by the image processing unit 5 and corresponding to a plurality of wavelengths. An example of obtaining a distribution of oxygen saturation as concentration distribution will be described below.

Assuming that light absorption other than by hemoglobin is negligibly low for the wavelength $\lambda_1$ and the wavelength $\lambda_2$, absorption coefficients for the wavelength $\lambda_1$ and the wavelength $\lambda_2$ are respectively represented by expressions (2) and (3) using a molar absorption coefficient of oxyhemoglobin and a molar absorption coefficient of deoxyhemoglobin.

[Math. 2]

$$\mu_a(\lambda_1) = \varepsilon_{ox}(\lambda_1) C_{ox} + \varepsilon_{de}(\lambda_1) C_{de} \quad (2)$$

$$\mu_a(\lambda_2) = \varepsilon_{ox}(\lambda_2) C_{ox} + \varepsilon_{de}(\lambda_2) C_{de} \quad (3)$$

In expressions (2) and (3), $\mu_a(\lambda_1)$ denotes an absorption coefficient of light with the wavelength $\lambda_1$ at a position (i, j, k) and $\mu_a(\lambda_2)$ denotes an absorption coefficient of light with the wavelength $\lambda_2$ at the position (i, j, k), both of which are measured in units of [mm$^{-1}$]. $C_{ox}$ denotes an amount [mol] of oxyhemoglobin and $C_{de}$ denotes an amount [mol] of deoxyhemoglobin. Both values correspond to the position (i, j, k).

$\varepsilon_{ox}(\lambda_1)$ and $\varepsilon_{de}(\lambda_1)$ respectively denote molar absorption coefficients [mm$^{-1}$mol$^{-1}$] of oxyhemoglobin and deoxyhemoglobin for the wavelength $\lambda_1$. $\varepsilon_{ox}(\lambda_2)$ and $\varepsilon_{de}(\lambda_2)$ respectively denote molar absorption coefficients [mm$^{-1}$mol$^{-1}$] of oxyhemoglobin and deoxyhemoglobin for the wavelength $\lambda_2$. $\varepsilon_{ox}(\lambda_1)$, $\varepsilon_{de}(\lambda_1)$, $\varepsilon_{ox}(\lambda_2)$, and $\varepsilon_{de}(\lambda_2)$ are obtained in advance by measurement or from literature values.

Therefore, $C_{ox}$ and $C_{de}$ are respectively obtained by solving the simultaneous equations represented by expressions (2) and (3) using molar absorption coefficients, $\mu_a(\lambda 1)$, and $\mu_a(\lambda_2)$. A least squares method may be used when a large number of wavelengths are to be used. In addition, as represented by expression (4) below, oxygen saturation SO$_2$ is defined as a proportion of oxyhemoglobin in total hemoglobin. Therefore, oxygen saturation SO$_2$ may be represented by expression (5) based on expressions (2), (3), and (4). Accordingly, using expression (5), the concentration distribution acquiring unit 9 can obtain oxygen saturation SO$_2$ at the position (i, j, k) based on the molar absorption coefficients, $\mu_a(\lambda_1)$, and $\mu_a(\lambda_2)$.

[Math. 3]

$$SO_2 = \frac{C_{ox}}{C_{ox} + C_{de}} \quad (4)$$

-continued $$SO_2 = \frac{\frac{\mu_a(\lambda_2)}{\mu_a(\lambda_1)} \cdot \varepsilon_{de}(\lambda_1) - \varepsilon_{de}(\lambda_2)}{(\varepsilon_{ox}(\lambda_2) - \varepsilon_{de}(\lambda_2)) - \frac{\mu_a(\lambda_2)}{\mu_a(\lambda_1)} \cdot (\varepsilon_{ox}(\lambda_1) - \varepsilon_{de}(\lambda_1))} \quad (5)$$

Figure 7:
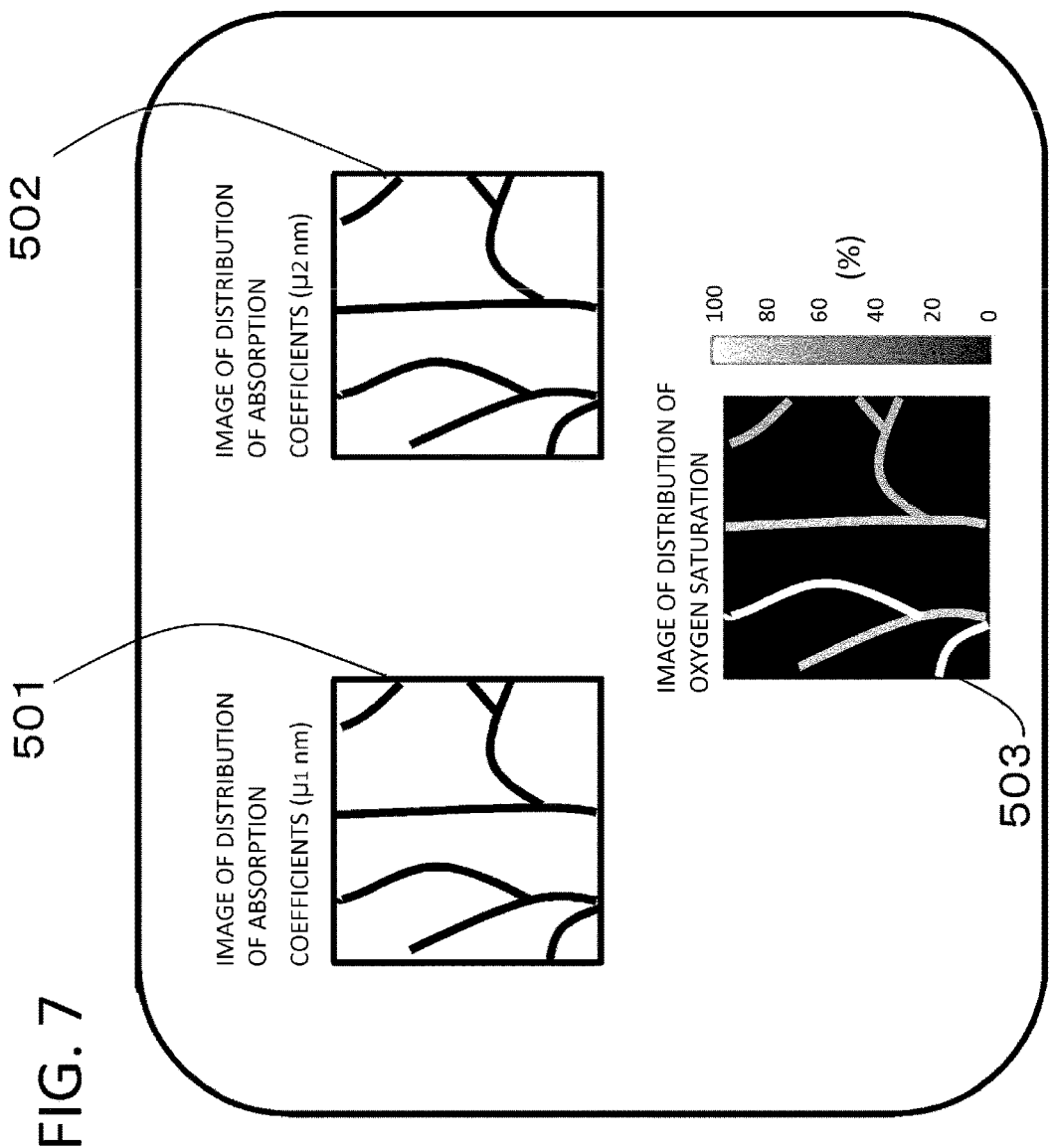
FIG. 7 is a schematic diagram showing an operation of a processor according to the embodiment.

A distribution of oxygen saturation can be acquired by performing this oxygen saturation acquisition process on each position. FIG. 7 shows an example of a display screen in a case where a distribution of oxygen saturation is obtained from the distribution of absorption coefficients of the wavelength $\lambda_1$ and the distribution of absorption coefficients of the wavelength $\lambda_2$. Reference numeral 501 denotes the distribution of absorption coefficients of the wavelength $\lambda_1$, reference numeral 502 denotes the distribution of absorption coefficients of the wavelength $\lambda_2$, and reference numeral 503 denotes an image of a distribution of oxygen saturation. The distribution of oxygen saturation may be three-dimensional data (set data of voxels) corresponding to a given region inside the object or two-dimensional data (set data of pixels) corresponding to one section in the three-dimensional data. In the diagram, an oxygen saturation value in a region where an absorber does not exist is set to 0% for the sake of convenience. In addition, since a distribution of oxygen saturation is obtained as a ratio of distributions of absorption coefficients, when the distributions of absorption coefficients for a plurality of wavelengths are relatively correct, a distribution of oxygen saturation can be appropriately obtained. Therefore, a distribution of absorption coefficients need not necessarily be accurately obtained as an absolute value. Furthermore, the processing may be ended by saving a distribution of oxygen saturation as data without actually displaying a screen as in the case of FIG. 7.

(Display Control Unit 6)

The display control unit 6 generates image data to be displayed by the display unit 7 based on the concentration distribution generated by the image processing unit 5 and the characteristic distribution acquiring unit generated by the characteristic distribution acquiring unit 4. Specifically, by setting the concentration distribution as a hue of an image and setting a normalized characteristic distribution normalized by a maximum value in the characteristic distribution as lightness, a concentration distribution weighted by the characteristic distribution can be displayed. In addition, display control such as arranging and displaying various display items together with the distribution data is performed.

Figure 8:
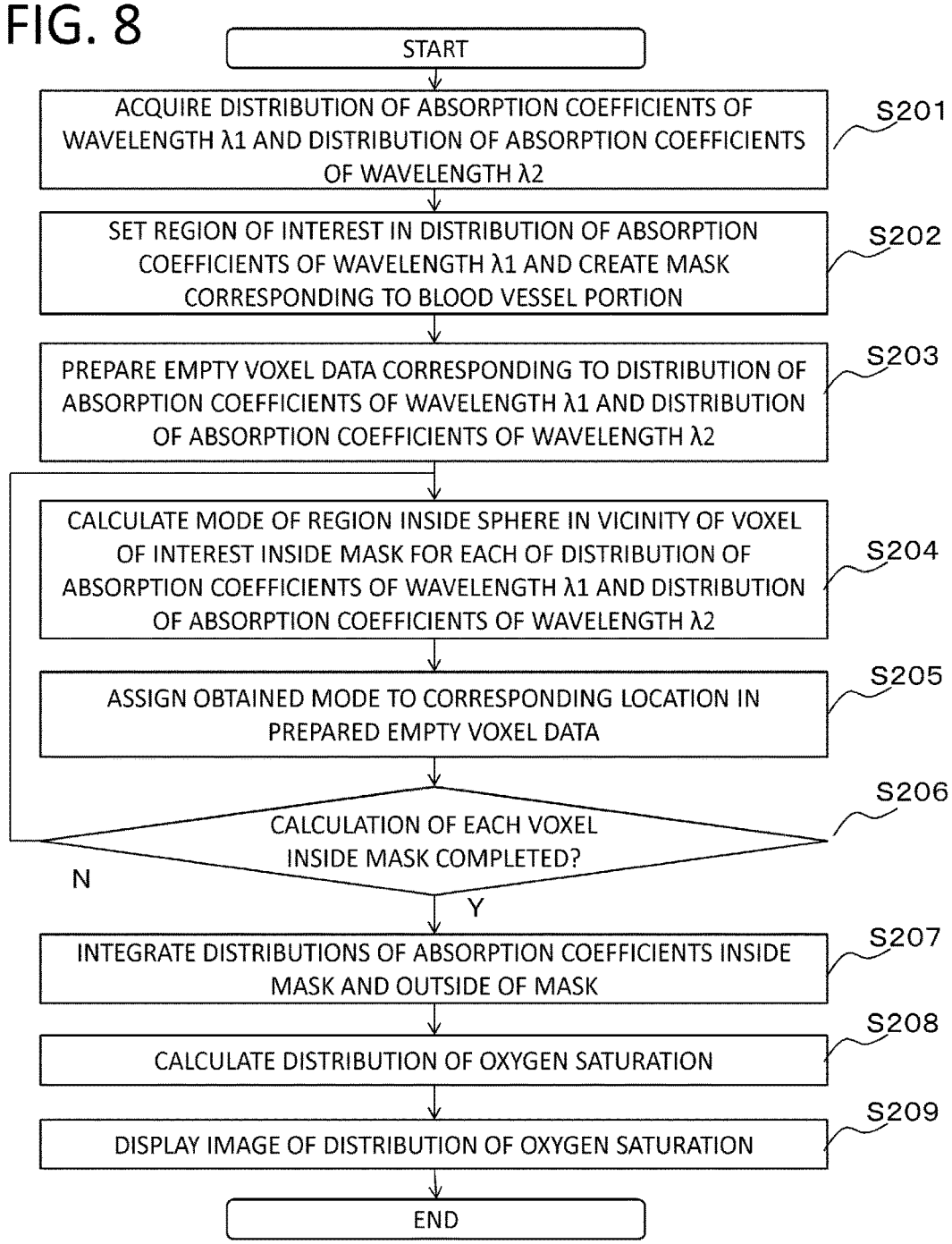
FIG. 8 is a flow chart showing an operation of a processor according to the embodiment.

FIG. 8 is a flow chart of the processor 40 according to the present embodiment. This flow starts in a state where received signals are sequentially input from the probe for each pulse of irradiated light to the signal collecting unit 8 in the processor 40 and processing such as A/D conversion and amplification has been performed by the signal collecting unit 8.

In step S201, the characteristic distribution acquiring unit 4 calculates a distribution of absorption coefficients of the wavelength $\lambda_1$ and a distribution of absorption coefficients of the wavelength $\lambda_2$ using received signals of the irradiated wavelength $\lambda_1$. In step S202, the image processing unit 5 sets a region of interest in the input distribution of absorption coefficients of the wavelength $\lambda_1$ and creates a mask with respect to a blood vessel portion. In step S203, empty voxel data for storing distributions of absorption coefficients of the wavelength $\lambda_1$ and the wavelength $\lambda_2$ after performing image processing is prepared. A size of the empty voxel data is equal to sizes of the absorption coefficients of the wavelength $\lambda_1$ and the wavelength $\lambda_2$.

In step S204, the image processing unit 5 focuses attention on one of the voxels in a masked data region in the region of interest in each of the distribution of absorption coefficients of the wavelength $\lambda_1$ and the distribution of absorption coefficients of the wavelength $\lambda_2$. A mode is calculated from voxels remaining after masking inside the region of interest among all voxel data within a certain distance from the voxel in focus. Intensity at which frequency is maximum frequency in an intensity histogram is used as the mode.

In step S205, respective modes of the absorption coefficient values of the wavelength $\lambda_1$ and the wavelength $\lambda_2$ obtained in S204 are assigned as substitute values to corresponding voxels in the three-dimensional voxel data prepared in S203. In step S206, a determination is made on whether or not processing in steps S204 and S205 have been completed. When processing has been completed on all voxels remaining after masking in the region of interest, a transition is made to next step S207. If not, a return is made to step S204.

In step S207, distributions in which the mode has been assigned to each voxel remaining after masking in the region of interest in each of the distribution of absorption coefficients of the wavelength $\lambda_1$ and the distribution of absorption coefficients of the wavelength $\lambda_2$ as well as other regions are integrated with the voxel data prepared in S203. In step S208, the concentration distribution acquiring unit 9 calculates a distribution of oxygen saturation based on data of the integrated distribution of absorption coefficients of the wavelength $\lambda_1$ and the integrated distribution of absorption coefficients of the wavelength $\lambda_2$. In step S209, the display control unit 6 displays the distribution of oxygen saturation calculated by the concentration distribution acquiring unit 9.

According to the processing, when calculating a distribution of oxygen saturation from distributions of absorption coefficients of a plurality of wavelengths, even when the distributions of absorption coefficients of the respective wavelengths contain noise or artifacts, the distributions of absorption coefficients can be acquired by reducing the effects of the noise and the like from signals inside a living organism structure region. As a result, a distribution of oxygen saturation for which the effect of noise or artifacts has been reduced can be calculated for a living organism structure region.

Moreover, while the concentration distribution acquiring unit 9 acquires a distribution of oxygen saturation as a concentration distribution in the example described above, the present embodiment is not limited thereto. As described earlier, any "distribution of values related to a concentration of a substance (a concentration distribution)" obtained using "a characteristic distribution based on light absorption" of a plurality of wavelengths may be acquired. In other words, a distribution of "weighted values of oxygen saturation", "total hemoglobin concentration", "oxyhemoglobin concentration", "deoxyhemoglobin concentration", "glucose concentration", "collagen concentration", "melanin concentration", or a "volume fraction" of fat or water may be acquired.

In addition, empty volume data corresponding to the distribution of absorption coefficients of the wavelength $\lambda_1$ and the distribution of absorption coefficients of the wavelength $\lambda_2$ is prepared in the example described above. However, one piece of empty volume data corresponding to the distribution of oxygen saturation may be prepared and a calculation result of oxygen saturation from the distributions of absorption coefficients of the two wavelengths calculated by the image processing unit 5 can be directly stored therein.

Furthermore, the characteristic distribution acquiring unit 4 acquires a distribution of absorption coefficients as a characteristic distribution based on light absorption in the example described above. However, the present embodiment is not limited thereto. For example, "a distribution of sound pressure (typically, a distribution of initial sound pressure)" or "a distribution of optical energy absorption density" may be acquired. For example, $\mu_a$ may be expressed as $P/(\Gamma \cdot \Phi)$ according to expression (1). Therefore, by substituting $\mu_a$ in expression (5) with $P/(\Gamma \cdot \Phi)$, oxygen saturation can be directly calculated from initial sound pressure. In other words, the concentration distribution acquiring unit 9 can directly acquire a distribution of oxygen saturation from a distribution of initial sound pressure without involving a distribution of absorption coefficients.

Figure 9:
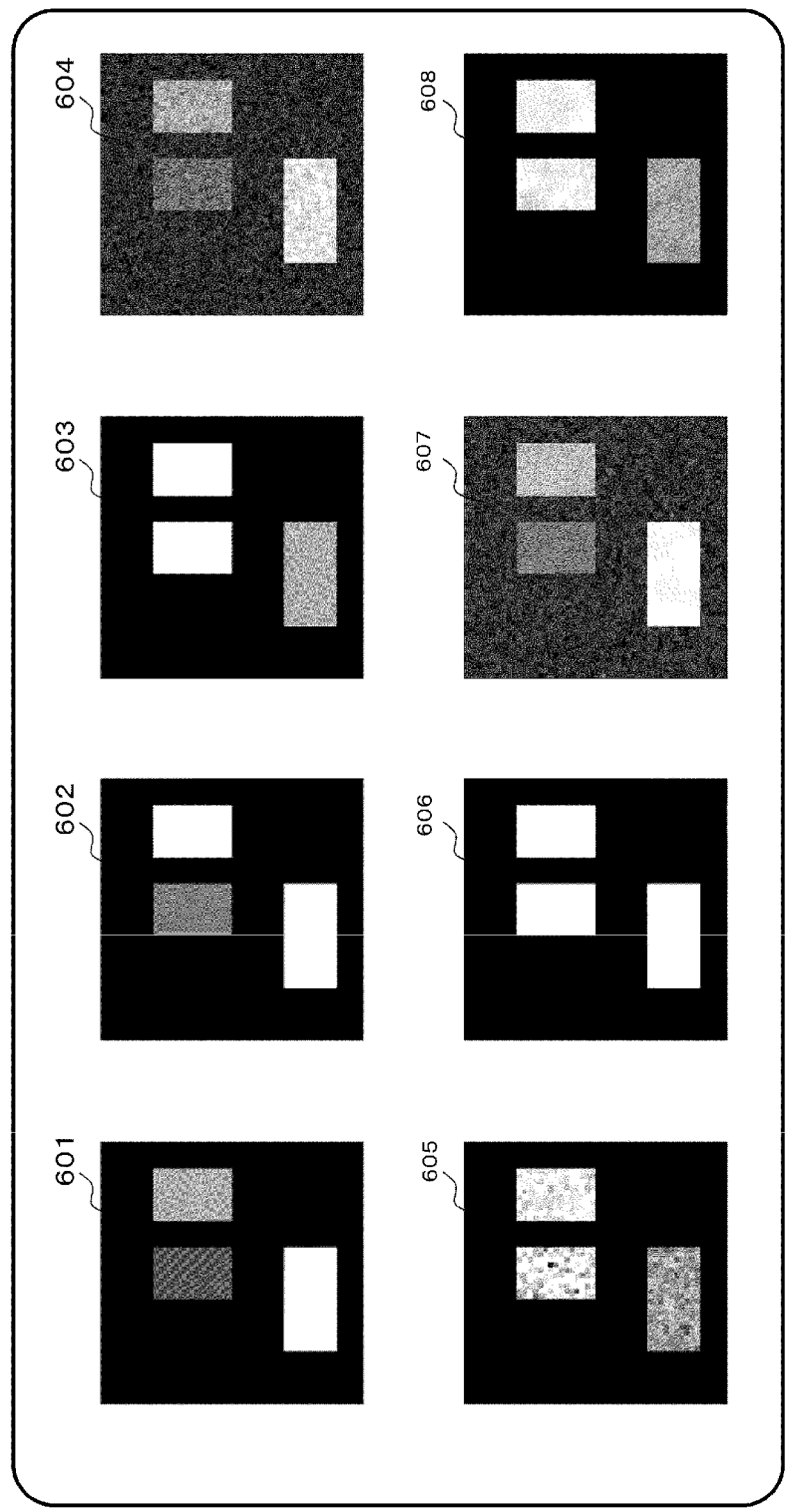
FIG. 9 is a schematic diagram showing an operation of a processor according to the embodiment.

FIG. 9 shows verification by a simulation using the present method. Reference numerals 601 and 602 respectively denote a distribution of absorption coefficients corresponding to two wavelengths (a first wavelength and a second wavelength). At this stage, noise is not included. In addition, each portion with high intensity simulates an absorber. Reference numeral 603 denotes oxygen saturation calculated from the distributions of absorption coefficients denoted by reference numerals 601 and 602. At this point, when displaying oxygen saturation, oxygen saturation may be displayed by setting a distribution normalized by maximum intensity of a distribution of absorption coefficients to lightness and oxygen saturation values to hue. However, in this case, oxygen saturation values of a masked absorber portion are displayed as a black-and-white image for the sake of convenience.

Reference numeral 604 denotes a distribution of absorption coefficients obtained by adding random Gaussian noise to the distribution of absorption coefficients denoted by reference numeral 601 (the first wavelength) for purposes of simulation. In a similar manner, random noise is also added to the distribution of absorption coefficients denoted by reference numeral 602 (the second wavelength) (not shown). Reference numeral 605 denotes a distribution of oxygen saturation calculated from the distributions of absorption coefficients obtained by adding random noise to the distributions of absorption coefficients denoted by reference numerals 601 and 602. At this point, variation in oxygen saturation due to the effect of noise is observed at each absorber.

Reference numeral 606 denotes a mask crated by setting a threshold to absorption coefficient intensity. Reference numeral 607 denotes a distribution obtained with respect to the first wavelength according to the method of the present invention. In this case, with respect to each voxel of a distribution of absorption coefficients in the mask, an average value is calculated using only voxels with intensity within a range of $3\sigma$ from an average value of specific values of the voxels among data within five voxels from each voxel. In other words, a weight may be adaptively determined in accordance with specific values of a voxel that is a substitution object and voxels in a periphery thereof. Accordingly, while intensity is averaged and the effect of noise is reduced in absorber portions, processing is not performed in portions other than the absorbers.

In addition, reference numeral 608 denotes a distribution of oxygen saturation calculated based on distributions of both the first wavelength and the second wavelength (not shown) after applying similar processing to that for reference numeral 607 to the second wavelength. This distribution of oxygen saturation also shows the effect of noise being reduced in absorber portions. As described above, with the method according to the present invention, the effects of noise and artifacts on a concentration distribution inside an object can be reduced and an image suitable for diagnosis can be displayed.

Third Embodiment

Figure 10:
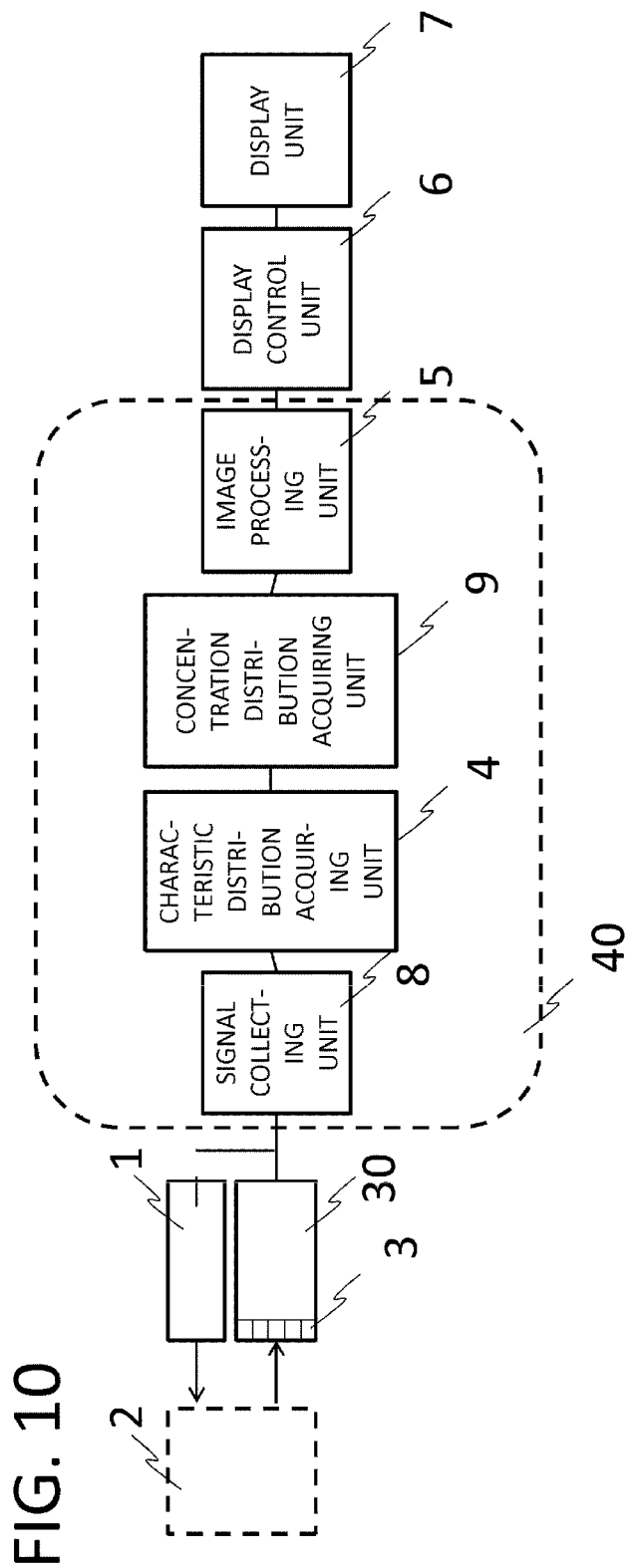
FIG. 10 is a schematic diagram showing a configuration of a photoacoustic apparatus according to still another embodiment.

Next, a third embodiment will be described. As shown in FIG. 10, the present embodiment differs from the second embodiment in an order of the concentration distribution acquiring unit 9 and the image processing unit 5 in the object information acquiring apparatus. In addition, there are portions of the contents of processing by the processor 40 that differ from the embodiment described above. Hereinafter, a description will be given with a focus on such differences.

With the object information acquiring apparatus according to the present embodiment, first, the concentration distribution acquiring unit 9 calculates a distribution of oxygen saturation based on a distribution of absorption coefficients calculated by the characteristic distribution acquiring unit 4. Subsequently, the image processing unit 5 performs statistical processing on intensity for each voxel of a masked concentration distribution. A weight of the distribution of absorption coefficients is used as a mask. Even when a binarization process as a mask is not performed, a distribution of oxygen saturation with reduced effects of noise and artifacts can be calculated. In addition, the entire distribution of absorption coefficients is set as a region of interest. Due to this processing, a calculation can be performed which increases weight of an oxygen saturation value in portions where absorber intensity is high such as a blood vessel and reduces weight of an oxygen saturation value in portions where absorber intensity is low such as noise. Furthermore, the effects of noise and artifacts can be further reduced by removing portions with extremely low weight and portions with high dispersion.

(Image Processing Unit 5)

The image processing unit 5 sets a mask on the concentration distribution output from the concentration distribution acquiring unit 9 and, after performing statistical processing based on data in the mask, performs mapping. In the following example, it is assumed that the concentration distribution is a distribution of oxygen saturation.

Figure 11:
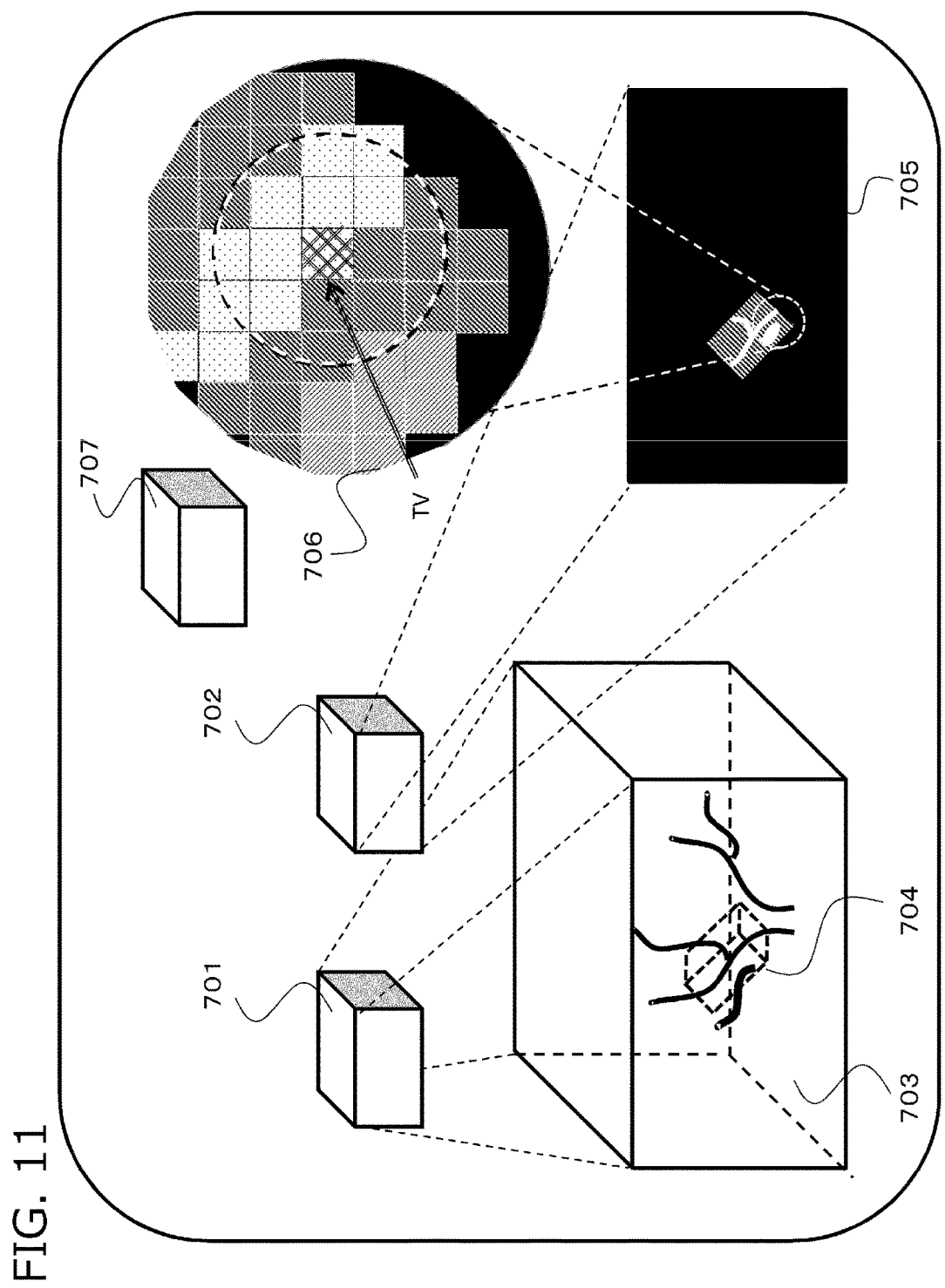
FIG. 11 is a schematic diagram showing an operation of a processor according to the embodiment.

In FIG. 11, reference numeral 701 denotes a three-dimensional distribution of oxygen saturation, and reference numeral 702 denotes a three-dimensional distribution of absorption coefficients of a wavelength $\lambda_1$ corresponding to the distribution of oxygen saturation. Reference numeral 703 denotes a conceptual diagram of the three-dimensional distribution of oxygen saturation and shows that oxygen saturation values are calculated in blood vessel portions. Reference numeral 704 denotes a region of interest set in a blood vessel portion such as a blood vessel. Reference numeral 705 denotes a side view of a mask with respect to the distribution of oxygen saturation denoted by reference numeral 704 representing a region of interest. In this case, unlike in the second embodiment, the inside of the region of interest of the mask is expressed by a weight calculated based on the distribution of absorption coefficients. In other words, in the inside of the region of interest, the whiter the color of a voxel, the higher the intensity of the voxel. A high-intensity region includes a region attributable to a living organism structure such as a blood vessel.

Reference numeral 706 denotes a partial enlarged view of the mask denoted by reference numeral 705. Reference numeral 707 denotes a three-dimensional distribution for storing a newly calculated distribution of oxygen saturation. In this case, the mask is created by setting a value of 0 outside the region of interest set in the distribution of absorption coefficients of the wavelength $\lambda_1$ and using a weight of intensity of a characteristic distribution as an internal value. As the weight of intensity of a characteristic distribution inside the region of interest, a weight normalized by a maximum value inside the region of interest is desirable. Alternatively, normalization may be performed by using intensity set by an operator or the apparatus as a maximum value and setting regions with values of 1 or larger to 1.

Next, a statistical processing method will be described. An oxygen saturation value of a voxel (denoted by reference character TV) shown shaded in a central part of a dotted circle in reference numeral 706 will now be described. The oxygen saturation value of the shaded voxel TV is obtained by a weighted-averaging process using an oxygen saturation value S of voxels inside a sphere with a certain radius from the voxel TV and a weight of the distribution of absorption coefficients. Specifically, when the total number of voxels inside the sphere is denoted by N, the oxygen saturation value of each voxel is denoted by Si (where i denotes a voxel number and i=1 to N), and a weight at a corresponding voxel in the mask created from the distribution of absorption coefficients is denoted by Wi (where i=1 to N), the oxygen saturation value of the shaded voxel TV is represented by expression (6) below.

[Math. 4]

$$S = \frac{\sum_{i=1}^{N} S_i \cdot W_i}{\sum_{i=1}^{N} W_i} \quad (6)$$

Accordingly, in the computation with respect to the voxel TV, the weight of an oxygen saturation value is increased in portions where absorber intensity is high such as a blood vessel and the weight of an oxygen saturation value is reduced in portions where absorber intensity is low such as noise. The obtained oxygen saturation value is assigned to a corresponding voxel in the distribution of oxygen saturation denoted by reference numeral 707. By similarly processing other voxels in the mask, substitute values in the mask are obtained. In the statistical processing, in the extracted voxel data, values equal to or smaller than a prescribed value may not be used to calculate the representative value or values with weights calculated from the distribution of absorption coefficients which are outside 3σ of the average value may be eliminated. As described above, with the image processing unit 5 according to the present embodiment, the effects of noise and artifacts can be reduced from a concentration distribution (a distribution of oxygen saturation) inside a mask.

Figure 12:
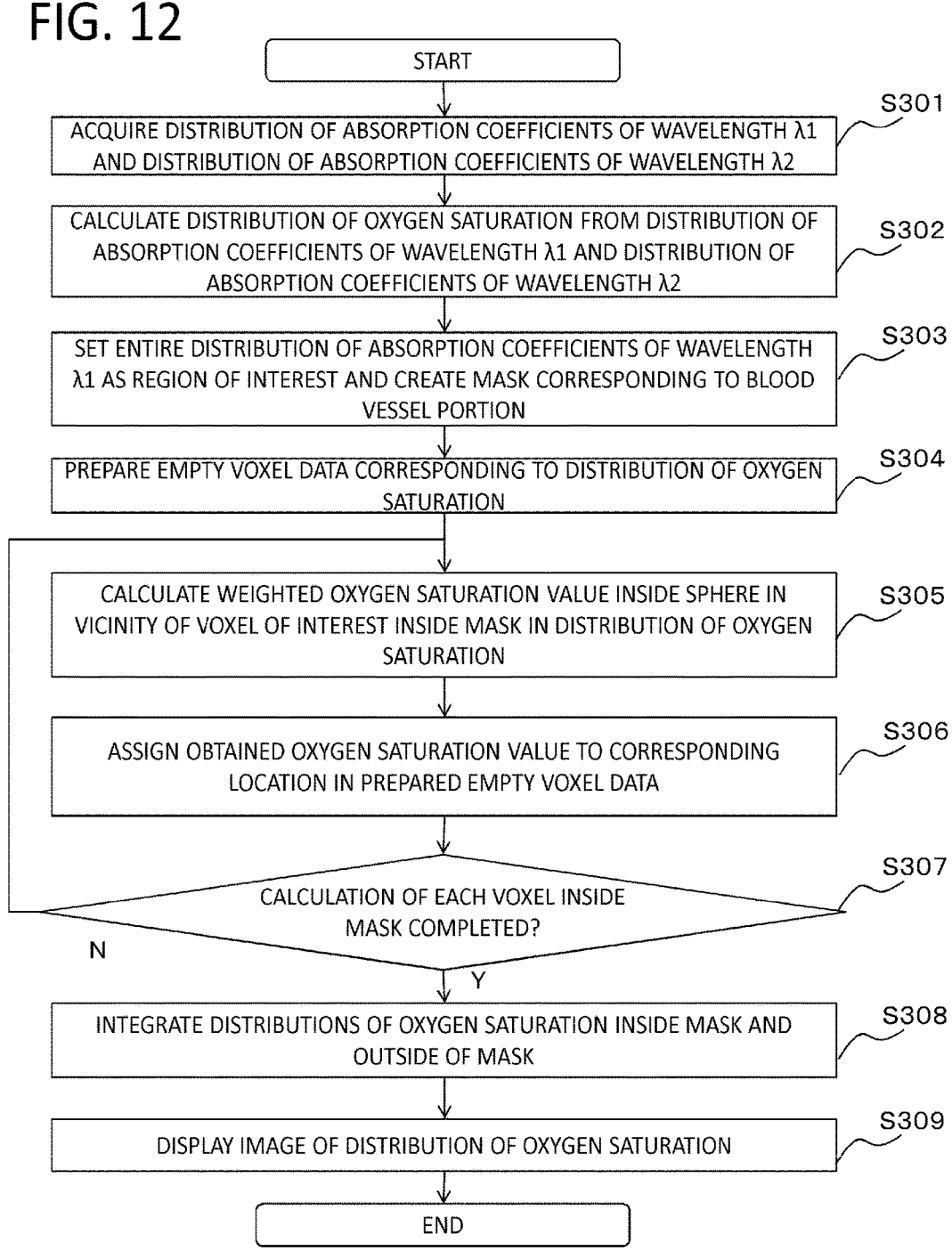
FIG. 12 is a flow chart showing an operation of a processor according to the embodiment.

FIG. 12 is a flowchart showing a processing flow of the processor 40 according to the present embodiment. In the present embodiment, a distribution of oxygen saturation with reduced effects of noise and artifacts is created. In doing so, an entire distribution of absorption coefficients is set as a region of interest.

In step S301, the characteristic distribution acquiring unit 4 calculates a distribution of absorption coefficients of the wavelength $\lambda_1$ and a distribution of absorption coefficients of the wavelength $\lambda_2$ using received signals of the irradiated wavelength $\lambda_1$. In step S302, the concentration distribution acquiring unit 9 calculates a distribution of oxygen saturation based on data of the distribution of absorption coefficients of the wavelength $\lambda_1$ and the distribution of absorption coefficients of the wavelength $\lambda_2$. In step S303, the image processing unit 5 sets the entire input distribution of absorption coefficients of the wavelength $\lambda_1$ as a region of interest and creates a mask with respect to a blood vessel portion.

In step S304, empty voxel data for storing a distribution of oxygen saturation after performing image processing is prepared. A size thereof is equal to a size of the distribution of oxygen saturation. In step S305, the image processing unit 5 focuses attention on one of the voxels in a masked data region in the distribution of oxygen saturation. A weighted oxygen saturation value is calculated from voxels remaining after masking among all voxel data within a certain distance from the voxel.

In step S306, the oxygen saturation value obtained in S305 is assigned to a corresponding voxel in the three-dimensional voxel data prepared in S304. In step S307, a determination is made on whether or not processing in steps S305 and S306 have been completed. When processing has been completed on all voxels remaining after masking in the region of interest, a transition is made to next step S308. If not, a return is made to step S305.

In step S308, a distribution of oxygen saturation calculated from data inside the mask and other regions are integrated with the voxel data prepared in S304 to create an integrated distribution of oxygen saturation. In step S309, the display control unit 6 displays the distribution of oxygen saturation calculated by the concentration distribution acquiring unit 9.

As described above, in the present embodiment, after a distribution of absorption coefficients calculated by the characteristic distribution acquiring unit 4 is handed over to the concentration distribution acquiring unit 9 and a distribution of oxygen saturation is calculated by the concentration distribution acquiring unit 9, the image processing unit 5 performs statistical processing on intensity for each voxel of a masked concentration distribution.

Figure 13:
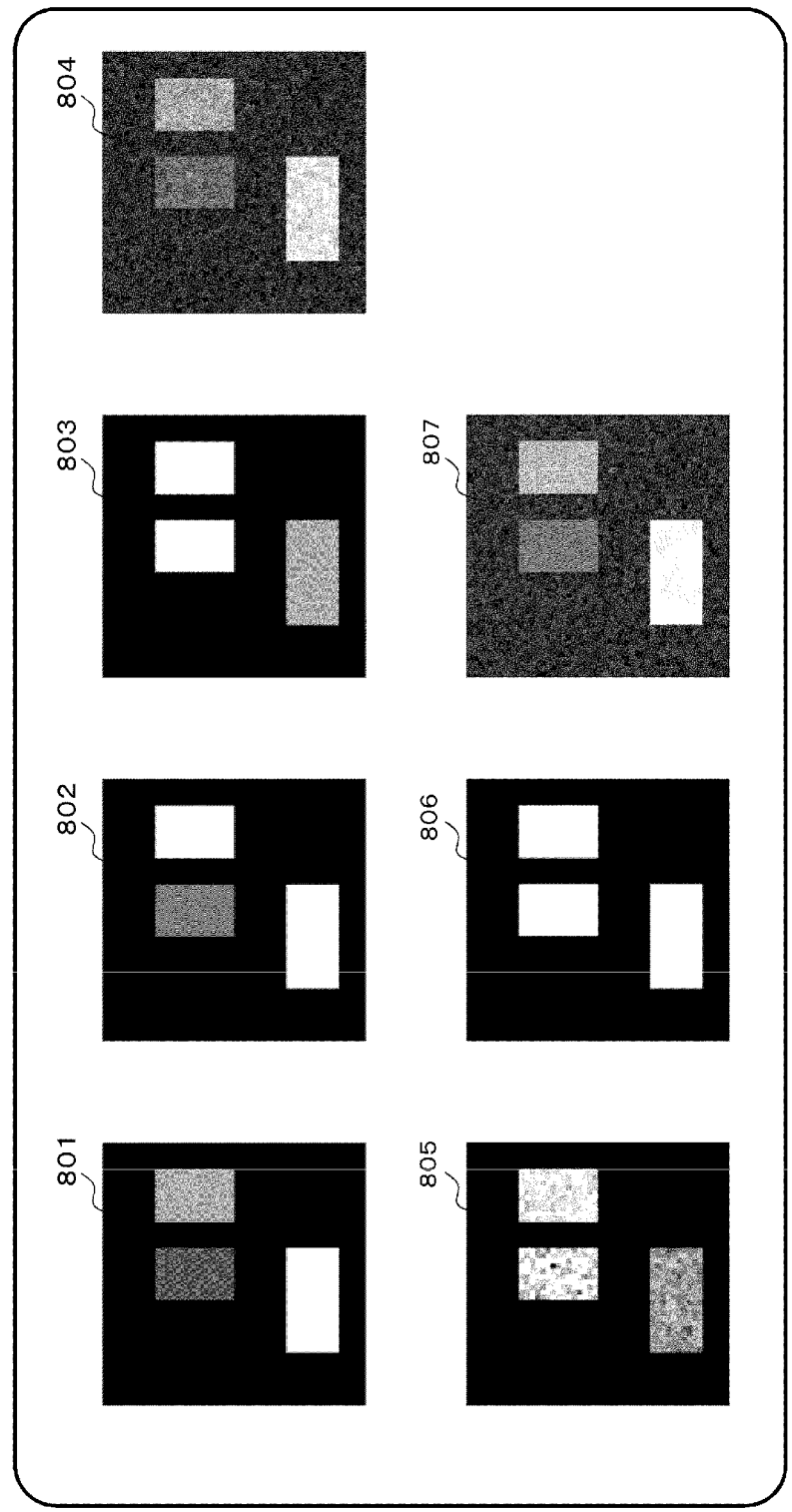
FIG. 13 is a schematic diagram showing an operation of a processor according to the embodiment.

FIG. 13 is a diagram showing verification by a simulation using the present method. Reference numerals 801 and 802 respectively denote distributions of absorption coefficients corresponding to two wavelengths. At this stage, noise is not included. In addition, each portion with high intensity simulates an absorber. A non-zero value is retained even for portions where intensity is not high. Reference numeral 803 denotes oxygen saturation calculated from the distributions of absorption coefficients denoted by reference numerals 801 and 802. In this case, the higher the oxygen saturation value, the higher the lightness and the whiter the representation. However, in the case of color image display, a weight distribution normalized by maximum intensity of the distribution of absorption coefficients may be assigned to lightness and an oxygen saturation value may be assigned to hue. In the present example, when imaging a distribution of oxygen saturation, a mask image due to a noise-added distribution of absorption coefficients described below is used instead of a weight distribution of lightness in consideration of characteristics of oxygen saturation values and grayscale.

Reference numeral 804 denotes a distribution of absorption coefficients obtained by adding random Gaussian noise to the distribution of absorption coefficients denoted by reference numeral 801. In a similar manner, random noise is also added to the distribution of absorption coefficients denoted by reference numeral 802 (not shown). Reference numeral 805 denotes a distribution of oxygen saturation calculated from the distributions of absorption coefficients of both wavelengths to which random noise has been added. Variation in oxygen saturation due to the effect of noise is observed inside each absorber.

Reference numeral 806 denotes a distribution of average values calculated from data within five voxels in the vicinity of each voxel in a distribution of oxygen saturation according to the present proposed method. In doing so, using voxels with oxygen saturation values within a range of $3\sigma$ from an average value, a weighted average value of oxygen saturation is calculated with a weight distribution obtained by normalizing a corresponding distribution of absorption coefficients with a maximum value thereof. Accordingly, it is shown that variation in oxygen saturation values has been reduced.

[Second Practical Example]

A more specific practical example will now be described. In the present practical example, a phantom simulating a breast is used as an object, light is irradiated through a holding member made of polymethylpentene which holds the object, and the probe 30 receives photoacoustic waves through the holding member. The probe 30 is a 2D probe including a plurality of conversion elements in a 1 MHz±40% frequency band.

In the present practical example, first, the object is irradiated with pulsed light having a wavelength of 797 nm from the light irradiating unit 1 and a photoacoustic wave is received by the probe 30. The processor 40 performs image reconstruction using universal back-projection based on the received signal. Accordingly, a three-dimensional distribution of initial sound pressure of one pulse is obtained. In the obtained distribution of initial sound pressure, only a region of a distribution of irradiated pulsed light has been reconstructed. The obtained distribution of initial sound pressure is constituted by 160 voxels vertically, 160 voxels horizontally, and 200 voxels in a height direction. A distribution of absorption coefficients can be calculated by correcting a light quantity distribution of the obtained distribution of initial sound pressure. In addition, the object is irradiated with pulsed light having a wavelength of 756 nm from the light irradiating unit 1, a photoacoustic wave is received by the probe 30, and a distribution of absorption coefficients is calculated by a similar processing method to that described above. In this case, an entire region is set as a region of interest and a mask.

Next, a distribution of oxygen saturation is calculated from the distributions of absorption coefficients of the two wavelengths described above. An entire distribution of oxygen saturation is set as a region of interest and a distribution obtained by normalizing intensity of a distribution of absorption coefficients is retained. With respect to voxels of interest in the distribution of oxygen saturation, a five voxel cubic in the vicinity of the voxels are extracted. An average value and a dispersion value are calculated in a distribution of absorption coefficients in a same region as the extracted region and data with a dispersion of $3\sigma$ or more from the average value is set to 0. In addition, a weighted oxygen saturation value is calculated using the distribution of absorption coefficients and the distribution of oxygen saturation and set as an oxygen saturation at the voxel of interest. Finally, a distribution is displayed in lightness in accordance with the oxygen saturation. Moreover, in a case of a color image, the image may be displayed by assigning the distribution of oxygen saturation to hue and assigning the distribution of absorption coefficients of 797 nm to lightness.

While absorption coefficient values are used after eliminating outliers when calculating an oxygen saturation value in the present practical example, processing such as setting a threshold to intensity of a distribution of absorption coefficients and not using data with low intensity may be performed. According to the present practical example, accuracy of calculation of an oxygen saturation value of a blood vessel portion is improved by performing image processing after calculating a distribution of oxygen saturation.

Other Embodiments

The present invention can also be realized by executing the processing described below. Specifically, the present invention can also be realized by supplying a program that realizes one or more functions of the respective embodiments described above to a system or an apparatus via a network or various storage media and having one or more processors in a computer of the system or the apparatus read and execute the program. Alternatively, the present invention can also be realized by a circuit (for example, an FPGA or an ASIC) which realizes one or more functions.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-166738, filed on Aug. 26, 2015, which is hereby incorporated by reference herein in its entirety.

What is claimed is:

1. An apparatus comprising:
a light irradiating unit configured to irradiate an object with light;
a receiving unit configured to output a signal in response to receiving an acoustic wave generated from the object irradiated with light; and
a processor configured to acquire characteristic distribution information, which indicates specific values at a plurality of positions inside the object, using the signal,
wherein the processor is configured to:
set a first position of interest;
acquire first weight distribution information which corresponds to the first position of interest and which is related to a plurality of positions including the first position of interest; and
acquire a substitute value for a specific value at the first position of interest using the first weight distribution information, the specific value at the first position of interest, and a specific value at a position that differs from the first position of interest among the plurality of positions.

2. The apparatus according to claim 1, wherein the processor is further configured to:
acquire a first weighted specific value at the first position of interest by weighting the specific value at the first position of interest using the first weight distribution information;
acquire a second weighted specific value at a position that differs from the first position of interest by weighting the specific value at the position that differs from the first position of interest using the first weight distribution information; and
acquire the substitute value at the first position of interest using the first weighted specific value and the second weighted specific value.

3. The apparatus according to claim 1, wherein the processor is further configured to:
set a second position of interest that differs from the first position of interest;
acquire second weight distribution information which corresponds to the second position of interest and which is related to a plurality of positions including the second position of interest; and
acquire a substitute value for a specific value at the second position of interest using the second weight distribution information, the specific value at the second position of interest, and a specific value at a position that differs from the second position of interest,
wherein the second weight distribution information differs from the first weight distribution information.

4. The apparatus according to claim 1, wherein the processor is further configured to determine the first position of interest using the weight distribution information.

5. The apparatus according to claim 1, wherein the processor is further configured to use a specific value at a position in a vicinity of the position of interest as the specific value at the position that differs from the position of interest when acquiring the substitute value.

6. The apparatus according to claim 1, wherein the specific value is an absorption coefficient for the light.

7. The apparatus according to claim 1, wherein the object is irradiated with light having a plurality of wavelengths, and
the processor is further configured to acquire a plurality of pieces of absorption coefficient distribution information corresponding to the plurality of wavelengths based on acoustic waves generated by the irradiation of the light having the plurality of wavelengths, and acquire oxygen saturation distribution information as the characteristic distribution information using the plurality of pieces of absorption coefficient distribution information.

8. The apparatus according to claim 7, wherein the processor is further configured to acquire the first weight distribution information based on any piece of absorption coefficient distribution information among the plurality of pieces of absorption coefficient distribution information.

9. The apparatus according to claim 2, wherein the processor is further configured to acquire a representative value of the first weighted specific value and the second weighted specific value as the substitute value.

10. The apparatus according to claim 9, wherein the representative value is any of a mean, a mode, and a median.

11. The apparatus according to claim 1, wherein the processor is further configured to set a position at which the specific value is larger than a threshold as the first position of interest using the characteristic distribution information.

12. The apparatus according to claim 1, wherein the processor is further configured to acquire the first weight distribution information based on a dispersion from the specific value at the first position of interest.

13. The apparatus according to claim 1, wherein the processor is further configured to acquire the first weight distribution information in which a weight at a position where a specific value is outside of a prescribed range among positions other than the first position of interest is set to zero.

14. The apparatus according to claim 13, wherein the processor is further configured to acquire the first weight distribution information in which a weight at a position where a specific value is outside $3\sigma$ of specific values at a plurality of positions including the first position of interest among positions other than the first position of interest is set to zero.

15. The apparatus according to claim 1, further comprising a display control unit configured to cause a display unit to display characteristic distribution information having been substituted with the substitute value.

16. The apparatus according to claim 1, wherein the processor is further configured to acquire information related to the first position of interest as determined based on an instruction issued by an operator and set the first position of interest using the information related to the first position of interest.

17. A method of processing using characteristic distribution information which is derived from an acoustic wave generated from an object irradiated with light and which indicates specific values at a plurality of positions inside the object, the acoustic wave being generated by an apparatus including a light irradiating unit, a receiving unit and a processor, the method comprising the steps of:
   setting a first position of interest;
   acquiring first weight distribution information which corresponds to the first position of interest and which is related to a plurality of positions including the first position of interest; and
   acquiring a substitute value for a specific value at the first position of interest using the first weight distribution information, the specific value at the first position of interest, and a specific value at a position that differs from the first position of interest.

18. A non-transitory storage medium storing a program that causes a computer to execute the method according to claim 17.

* * * * *